United States Patent
Coursey et al.

(10) Patent No.: US 9,919,314 B2
(45) Date of Patent: Mar. 20, 2018

(54) AIR COOLING SYSTEMS AND METHODS FOR MICROFLUIDIC DEVICES

(71) Applicant: Canon U.S. Life Sciences, Inc., Rockville, MD (US)

(72) Inventors: Johnathan S. Coursey, Germantown, MD (US); Kenton C. Hasson, Germantown, MD (US); Ben Lane, Hydes, MD (US); Eric Schneider, Catonsville, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 205 days.

(21) Appl. No.: 14/923,058

(22) Filed: Oct. 26, 2015

(65) Prior Publication Data

US 2016/0038945 A1 Feb. 11, 2016

Related U.S. Application Data

(62) Division of application No. 13/222,565, filed on Aug. 31, 2011, now Pat. No. 9,168,529.

(Continued)

(51) Int. Cl.
*B01L 3/00* (2006.01)
*B01L 7/00* (2006.01)
(Continued)

(52) U.S. Cl.
CPC .............. *B01L 7/52* (2013.01); *C12P 19/34* (2013.01); *F28F 9/02* (2013.01); *G01N 35/08* (2013.01);
(Continued)

(58) Field of Classification Search
CPC ......... B01L 2200/027; B01L 2200/028; B01L 2200/147; B01L 2300/041; B01L 2300/06;
(Continued)

(56) References Cited

U.S. PATENT DOCUMENTS 6,330,154 B1  12/2001  Fryers et al.
6,443,216 B1   9/2002  Lombard et al.
(Continued)

FOREIGN PATENT DOCUMENTS

WO   89/12502 A1   12/1989
WO   95/11294 A1    4/1995
(Continued)

OTHER PUBLICATIONS

Kopp et al., "Chemical Amplification: Continuous-Flow PCR on a Chip," Science, 280(15), pp. 1046-1048 (1998).
(Continued)

*Primary Examiner* — Jennifer Wecker
(74) *Attorney, Agent, or Firm* — Rothwell, Figg, Ernst & Manbeck, P.C.

(57) ABSTRACT

Systems and methods for air cooling a microfluidic device using confinement channels to isolate cooling air from exposed liquids are disclosed. The systems and methods may also thermally condition the cooling airflow for improved robustness of the microfluidic device. In one embodiment, the air cooling system includes a split-level cooling manifold including an inlet duct that directs cooling air to a microfluidic device and an outlet duct that directs air heated by the microfluidic device away from the microfluidic device. The temperature of cooling air may be measured. The cooling air may be preheated to a temperature that is higher than an expected ambient temperature. The temperature of the cooling air after being heated by a microfluidic device may be measured.

15 Claims, 28 Drawing Sheets

Related U.S. Application Data

(60) Provisional application No. 61/378,467, filed on Aug. 31, 2010, provisional application No. 61/487,265, filed on May 17, 2011.

(51) Int. Cl.

| | |
|---|---|
| *F28F 9/02* | (2006.01) |
| *C12M 1/40* | (2006.01) |
| *C12P 19/34* | (2006.01) |
| *G01N 35/08* | (2006.01) |
| *C07H 1/06* | (2006.01) |
| *C07H 21/04* | (2006.01) |
| *G01N 35/00* | (2006.01) |

(52) U.S. Cl.
CPC ... *B01L 2200/027* (2013.01); *B01L 2200/028* (2013.01); *B01L 2200/147* (2013.01); *B01L 2300/041* (2013.01); *B01L 2300/06* (2013.01); *B01L 2300/18* (2013.01); *B01L 2300/1805* (2013.01); *B01L 2300/1838* (2013.01); *B01L 2300/1844* (2013.01); *B01L 2300/1883* (2013.01); *B01L 2300/1894* (2013.01); *G01N 2035/00346* (2013.01); *Y02P 20/129* (2015.11)

(58) Field of Classification Search
CPC ......... B01L 2300/18; B01L 2300/1805; B01L 2300/1838; B01L 2300/1844; B01L 2300/1883; B01L 2300/1894; B01L 7/52; C12P 19/34; F28F 9/02; G01N 2035/00346; G01N 35/08; Y02P 20/129
See application file for complete search history.

(56) References Cited

U.S. PATENT DOCUMENTS

| | | | |
|---|---|---|---|
| 6,657,169 B2 * | 12/2003 | Brown | B01L 7/52 219/385 |
| 6,960,437 B2 | 11/2005 | Enzelberger et al. | |
| 6,986,837 B2 | 1/2006 | Chow et al. | |
| 7,032,392 B2 | 4/2006 | Koeneman et al. | |
| 7,629,124 B2 | 12/2009 | Hasson et al. | |
| 7,763,973 B1 | 7/2010 | Bratkovski et al. | |
| 2002/0151039 A1 | 10/2002 | Wittwer et al. | |
| 2003/0148922 A1 | 8/2003 | Knapp et al. | |
| 2005/0042639 A1 | 2/2005 | Knapp et al. | |
| 2006/0180300 A1 | 8/2006 | Lenehan et al. | |
| 2006/0246573 A1 | 11/2006 | Kurane et al. | |
| 2006/0278373 A1 | 12/2006 | Hsu | |
| 2006/0292601 A1 | 12/2006 | Tam | |
| 2007/0048154 A1 | 3/2007 | Sapir | |
| 2008/0038163 A1 | 2/2008 | Boege et al. | |
| 2008/0124723 A1 | 5/2008 | Dale et al. | |
| 2009/0022625 A1 * | 1/2009 | Lee | B01L 7/52 422/68.1 |
| 2009/0084530 A1 | 4/2009 | Shuy | |
| 2009/0130719 A1 | 5/2009 | Handique | |
| 2009/0134046 A1 | 5/2009 | Breidenthal et al. | |
| 2009/0136804 A1 | 5/2009 | Bono | |
| 2009/0238751 A1 | 9/2009 | Wilhite et al. | |
| 2009/0253181 A1 | 10/2009 | Vangbo et al. | |
| 2010/0035358 A1 | 2/2010 | Lehto et al. | |
| 2011/0300230 A1 | 12/2011 | Peterson et al. | |
| 2012/0011921 A1 | 1/2012 | Broeckhoven et al. | |

FOREIGN PATENT DOCUMENTS

| | | |
|---|---|---|
| WO | 01/08801 A1 | 2/2001 |
| WO | 2005/075683 A1 | 8/2005 |

OTHER PUBLICATIONS

Lagally et al., "Single-Molecule DNA Amplification and Analysis in an Integrated Microfluidic Device," Analytical Chemistry, 73(3), pp. 565-570 (2001).

Park et al., "Cylindrical compact thermal-cycling device for continuous-flow polymerase chain reaction," Analytical Chemistry, 75, pp. 6029-6033 (2003).

* cited by examiner

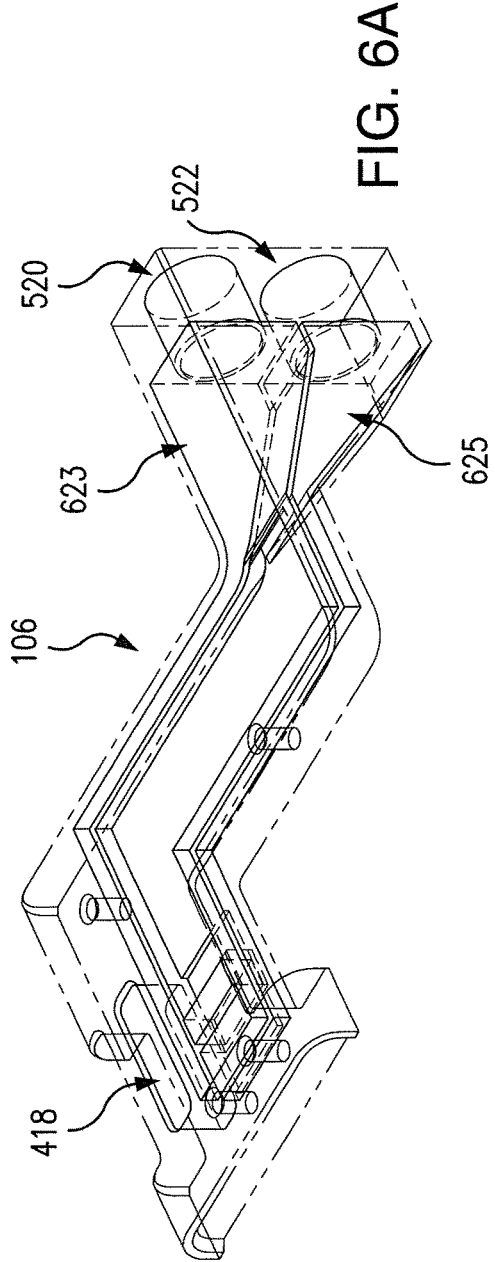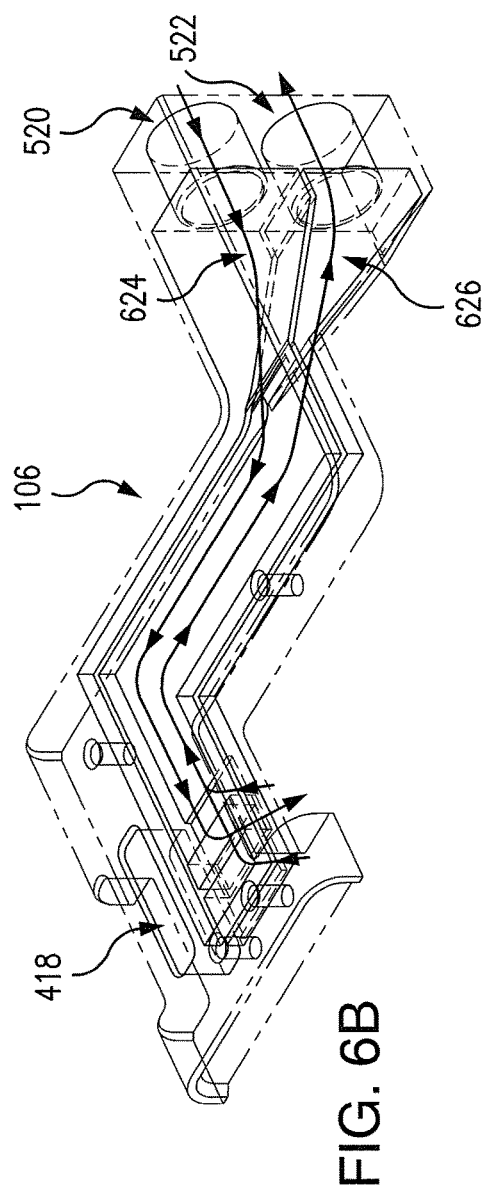

AIR COOLING SYSTEMS AND METHODS FOR MICROFLUIDIC DEVICES

CROSS-REFERENCE TO RELATED APPLICATION

The present application is a divisional of U.S. patent application Ser. No. 13/222,565, filed on Aug. 31, 2011, which claims the benefit of priority to U.S. Provisional Application Ser. No. 61/378,467, filed on Aug. 31, 2010, and U.S. Provisional Application Ser. No. 61/487,265, filed on May 17, 2011, each of which is incorporated herein by reference in their entireties.

BACKGROUND

Field of Invention

The present invention relates to air cooling systems and methods for microfluidic devices. More specifically, aspects of this invention relate to air cooling systems and methods that isolate the cooling air from exposed liquids by using confinement channels. The invention also relates to thermal conditioning of the cooling airflow for improved robustness of the microfluidic device.

Discussion of the Background

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, identification of crime scene features, the ability to propagate industrial organisms and many other techniques. Determination of the integrity of a nucleic acid of interest can be relevant to the pathology of an infection or cancer.

One of the most powerful and basic technologies to detect small quantities of nucleic acids is to replicate some or all of a nucleic acid sequence many times, and then analyze the amplification products. Polymerase chain reaction (PCR) is a well-known technique for amplifying deoxyribonucleic acid (DNA). With PCR, one can produce millions of copies of DNA starting from a single template DNA molecule. PCR includes phases of "denaturation," "annealing," and "extension." These phases are part of a cycle which is repeated a number of times so that at the end of the process there are enough copies to be detected and analyzed. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

The PCR process phases of denaturing, annealing, and extension occur at different temperatures and cause target DNA molecule samples to replicate themselves. Temperature cycling (thermocyling) requirements vary with particular nucleic acid samples and assays. In the denaturing phase, a double stranded DNA (dsDNA) is thermally separated into single stranded DNA (ssDNA). During the annealing phase, primers are attached to the single stranded DNA molecules. Single stranded DNA molecules grow to double stranded DNA again in the extension phase through specific bindings between nucleotides in the PCR solution and the single stranded DNA. Typical temperatures are 95° C. for denaturing, 55° C. for annealing, and 72° C. for extension. The temperature is held at each phase for a certain amount of time which may be a fraction of a second up to a few tens of seconds. The DNA is doubled at each cycle, and it generally takes 20 to 40 cycles to produce enough DNA for certain applications. To have good yield of target product, one has to accurately control the sample temperatures at the different phases to a specified degree.

More recently, a number of high throughput approaches to performing PCR and other amplification reactions have been developed, e.g., involving amplification reactions in microfluidic devices, as well as methods for detecting and analyzing amplified nucleic acids in or on the devices. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones. See, for example, Lagally et al. (*Analytical Chemistry* 73:565-570 (2001)), Kopp et al. (*Science* 280:1046-1048 (1998)), Park et al. (*Analytical Chemistry* 75:6029-6033 (2003)), Hahn et al. (WO 2005/075683), Enzelberger et al. (U.S. Pat. No. 6,960,437) and Knapp et al. (U.S. Patent Application Publication No. 2005/0042639).

Many detection methods require a determined large number of copies (millions, for example) of the original DNA molecule, in order for the DNA to be characterized. Because the total number of cycles is fixed with respect to the number of desired copies, the only way to reduce the process time is to reduce the length of a cycle. Thus, the total process time may be significantly reduced by rapidly heating and cooling samples to process phase temperatures while accurately maintaining those temperatures for the process phase duration.

A variety of cooling techniques exist for PCR and other (i.e., non-PCR) systems. Many existing techniques involve liquid coolants. Another technique uses a series of microdevices, built from moveable filaments of titanium-coated silicon, mounted above a surface of the same material. The temperature of the device is monitored by constantly measuring its output resistance. When the temperature exceeds a set level, the device is moved, using electrostatic actuation, so that it touches the silicon. By periodically placing the device in contact with its underlying substrate, its thermal conductivity can be changed and its temperature controlled.

In yet another technique, one or more MEMS microchannel volumes are in communication with one or more MEMS micro-pump assemblies. Each micro-pump assembly is comprised of a flexure valve, such as a leaf valve, and means to drive a coolant through the channel volumes, such as an electrostatic interleaved comb drive structure.

Liquid cooling systems are very effective at removing heat although they are not practical because the liquid must be contained and may be dangerous. Pumping systems are expensive and prone to reliability issues. Air cooling is attractive, but existing systems have not resolved several issues, including effectively delivering air to a microsystem, ensuring that airflow produces consistent cooling, preventing airflow from having a negative effect on the thermal calibration of the microdevice, and isolating the airflow from exposed liquids (e.g., reagents) in a medical device.

Accordingly, there is a need in the art for a cooling system capable of effectively cooling a microfluidic device.

SUMMARY

The present invention relates to microfluidic device and a comprehensive air cooling systems and methods for microfluidic devices. More specifically, this invention relates to effective air delivery systems and methods capable of cooling a microfluidic device without disturbing other liquids present in the system (e.g., reagents in a medical device). The invention also relates to systems for thermally conditioning the air-flow to improve system robustness and aid thermal calibration.

In one aspect, the present invention provides an instrument comprising a microfluidic device and a cooling manifold. In one embodiment, the microfluidic device includes one or more microfluidic channels, one or more inlet ports, one or more outlet ports and one or more heat sinks. The cooling manifold is configured to direct an airflow to the one or more heat sinks of the microfluidic device while isolating the airflow from the one or more inlet ports of the microfluidic device. The cooling manifold may include an air inlet configured to receive the airflow, an air outlet, and an inlet duct configured to direct the airflow from the air inlet to the one or more heat sinks of the microfluidic device.

The instrument may comprise an outlet duct configured to direct airflow from the one or more heat sinks away from the microfluidic device. At least a portion of the outlet duct may be underneath the inlet duct. At least a portion of the inlet duct may be underneath the outlet duct.

In one embodiment of the invention, the cooling manifold may be a bi-level cooling manifold including a first duct and a second duct. The first duct may include the upper confinement channel and a vertical channel connected to the upper confinement channel. The second duct may include a lower confinement channel and an opening. At least a portion of the lower confinement channel may be underneath the upper confinement channel. One of the first duct and the second duct may be the inlet duct.

In another embodiment of the invention, the cooling manifold may be a clamshell cooling manifold including a first piece, a second piece, a compartment, an inlet opening, an inlet duct and an outlet opening. The compartment may be configured for insertion and removal of the microfluidic device. The compartment may be formed in the first piece, the second piece or both the first piece and the second piece. The inlet opening may be configured to receive an airflow. The inlet duct may be configured to direct the airflow from the inlet opening to one or more heat sinks of a microfluidic device that has been inserted into the compartment. The outlet opening may be configured to output the airflow from the cooling manifold after the airflow has been directed to one or more heat sinks of a microfluidic device that has been inserted into the compartment.

In some embodiments, the instrument may comprise a temperature measuring device configured to measure a temperature of the airflow in the inlet duct. The instrument may also comprise a thermal controller configured to determine a temperature of the microfluidic device based on the temperature measured by the temperature measuring device. The thermal controller may be configured to correct cooling and/or heating times or calibration equations based on the determined temperature of the microfluidic device. The temperature measuring device may be located within the cooling manifold where the airflow leaves the inlet duct. The instrument may comprise: an outlet duct configured to direct airflow from the one or more heat sinks away from the microfluidic device; a first temperature measuring device configured to measure a temperature of the airflow in the inlet duct; and a second temperature measuring device configured to measure a temperature of the airflow in the outlet duct. The instrument may comprise a thermal controller configured to determine an amount of power removed from the microfluidic device based on the difference between the temperature measured by the first temperature measuring device and the temperature measured by the second temperature measuring device.

The instrument may comprise a blower and an input duct interfaced with the blower and configured to direct airflow from the blower to the inlet of the cooling manifold. The instrument may comprise a rear enclosure containing the blower. The blower may be configured to draw air from outside the instrument. The microfluidic device may be configured to perform polymerase chain reaction (PCR) and/or thermal melt analysis and/or DNA extraction. The instrument may comprise a liquid handling system. The liquid handling system may include one or more robotic pipettors. The instrument may comprise a heat exchanger configured to preheat the airflow directed to the one or more heat sinks by the inlet duct to a temperature higher than a temperature range within which an ambient temperature of an environment of the instrument is expected to remain. The instrument may comprise a temperature controller configured to control the preheating performed by the heat exchanger.

Another aspect of the present invention is a bi-level cooling manifold for cooling a microfluidic device having one or more microfluidic channels, one or more inlet ports, one or more outlet ports and one or more heat sinks. The cooling manifold comprises a first duct and a second duct. The first duct may include an upper confinement channel and a vertical channel connected to the upper confinement channel. The second duct may include a lower confinement channel and an opening. In one embodiment, at least a portion of the lower confinement channel is underneath the upper confinement channel. The cooling manifold is configured to isolate airflow in the first and second ducts from the one or more inlet ports of the microfluidic device.

The cooling manifold may be configured to isolate the airflow in the first and second ducts from the one or more outlet ports of the microfluidic device. The vertical channel of the first duct may extend through the lower confinement chamber of the second duct. The opening may comprise a first opening and a second opening, and the first opening and the second opening may be on opposite sides of the vertical channel of the first duct.

In one embodiment, the first duct may be an inlet duct including an inlet, and the second duct may be an outlet duct including an outlet. The inlet and the outlet may have a vertical relationship in which the inlet is disposed above the outlet. The inlet and the outlet may have a horizontal relationship in which the inlet is displaced in the horizontal direction relative to the outlet.

In another embodiment, the first duct may be an outlet duct including an outlet, and the second duct may be an inlet duct including an inlet. The inlet and the outlet may have a vertical relationship in which the outlet is disposed above the inlet. The inlet and the outlet may have a horizontal relationship in which the inlet is displaced in the horizontal direction relative to the outlet.

In some embodiments, the cooling manifold may comprise a port configured to allow fluid interface with the one or more inlet ports of the microfluidic device. The port may be configured to allow fluid interface with the one or more outlet ports of the microfluidic device. One of the first and second ducts may be an inlet duct, and the cooling manifold may further comprise a temperature measuring device configured to measure a temperature of the airflow in the inlet duct. The temperature measuring device may be located within the inlet duct where the airflow leaves the inlet duct.

The first duct may be the inlet duct, and the temperature measuring device may be located within the vertical channel of the first duct where the airflow leaves the vertical channel. The cooling manifold may comprise a first temperature measuring device configured to measure a temperature of the airflow in the first duct and a second temperature measuring device configured to measure a temperature of the airflow in the second duct. The first duct may be an inlet duct, and the airflow in the first duct may leave the first duct through the vertical channel. The second duct may be an outlet duct, and the airflow in the second channel may enter the second channel through the opening. The first temperature measuring device may be located within the vertical channel of the first duct where the airflow leaves the vertical channel, and the second measuring device may be located within the lower confinement channel where the airflow in the second channel enters through the opening.

In yet another aspect, the present invention provides a method for air cooling a microfluidic device having one or more microfluidic channels, one or more inlet ports, one or more outlet ports and one or more heat sinks. In one embodiment, the method may comprise: receiving cooling air through an inlet of a first duct of a bi-level cooling manifold, using the first duct of the cooling manifold to isolate the cooling air from the one or more inlet ports of the microfluidic device, directing the cooling air to a vertical channel of the first duct of the cooling manifold using an upper confinement channel of the first duct of the cooling manifold, directing the cooling air to the one or more heat sinks of the microfluidic device using the vertical channel of the first duct of the cooling manifold, heating the cooling air using the heat sinks of the microfluidic device, directing the heated air into a lower confinement channel of a second duct of the cooling manifold using an opening of the second duct of the cooling manifold, using the second duct of the cooling manifold to isolate the heated air from the one or more inlet ports of the microfluidic device, and directing the heated air to an outlet of the second duct using the lower confinement channel.

In some embodiments, the method may comprise using the first duct of the cooling manifold to isolate the cooling air from the one or more outlet ports of the microfluidic device, and using the second duct of the cooling manifold to isolate the heated air from the one or more outlet ports of the microfluidic device. The vertical channel of the first duct may extend through the lower confinement chamber of the second duct. The opening may comprise a first opening and a second opening, the first opening and the second opening may be on opposite sides of the vertical channel of the first duct, and the directing the heated air to the outlet of the second duct using the lower confinement channel may comprise directing a portion of the heated air that enters one of the first and second openings of the second duct around the vertical channel of the first duct.

The method may comprise delivering one or more liquids to the one or more inlet ports through a port of the bi-level cooling manifold. The method may comprise measuring a temperature of the cooling air in the first duct. The temperature of the cooling air may be measured as the cooling air leaves the vertical channel of the first duct. The method may comprise measuring a temperature of the heated air in the second duct. The temperature of the cooling air is measured as the cooling air leaves the vertical channel of the first duct, and the temperature of the heated air may be measured as the heated air enters the opening of the second duct. The method may comprise determining an amount of power removed from the microfluidic device based on the difference between the temperature of the cooling air and the temperature of the heated air.

In some embodiments, the method may comprise determining a temperature of the microfluidic device based on the measured temperature of the cooling air in the first duct. The method may comprise correcting cooling and/or heating times and/or calibration equations of the microfluidic device based on the determined temperature of the microfluidic device. The method may comprise preheating the cooling air to a temperature higher than a temperature range within which an ambient temperature is expected to remain.

In still another aspect, the present invention may provide a clamshell cooling manifold for cooling a microfluidic device. In one embodiment, the cooling manifold may comprise: a first piece, a second piece, a compartment, an inlet opening, an inlet duct, and an outlet opening. The compartment may be configured for insertion and removal of a microfluidic device having one or more heat sinks. The compartment may be formed in the first piece, the second piece or both the first piece and the second piece. The inlet opening may be configured to receive an airflow. The inlet duct may be configured to direct the airflow from the inlet opening to one or more heat sinks of a microfluidic device that has been inserted into the compartment. The outlet opening may be configured to output the airflow from the cooling manifold after the airflow has been directed to one or more heat sinks of a microfluidic device that has been inserted into the compartment.

In one embodiment, the first piece may include the inlet opening, the inlet duct and the outlet opening. The first piece may be a top piece, and the second piece may be a bottom piece below the top piece. The cooling manifold may be configured to output the airflow from the cooling manifold in a substantially horizontal direction. The inlet duct may be a rectangular inlet duct. The inlet opening may be configured to attach to an input duct having a circular cross-section. The first and second piece may be configured to be fixed together.

In one embodiment, the inlet duct may be configured to direct airflow in a substantially horizontal direction across one or more heat sinks of a microfluidic device that has been inserted into the compartment. In another embodiment, the inlet duct may be configured to direct airflow to impinge downwardly on one or more heat sinks of a microfluidic device that has been inserted into the compartment. Further, the inlet duct may be configured to direct airflow to impinge downwardly in a substantially vertical direction on one or more heat sinks of a microfluidic device that has been inserted into the compartment.

In another aspect, the present invention provides a method for air cooling a microfluidic device having one or more microfluidic channels, one or more inlet ports, one or more outlet ports and one or more heat sinks. In one embodiment, the method may comprise receiving an airflow at an inlet opening of the cooling manifold, directing the airflow from the inlet opening to the one or more heat sinks of the microfluidic device, heating the airflow using the heat sinks of the microfluidic device, and outputting the heated airflow from the cooling manifold through an outlet opening. In one embodiment, the microfluidic device may have been inserted into a compartment of the cooling manifold, and the compartment may be formed in a first piece of the cooling manifold, a second piece or both the first piece and the second piece of the cooling manifold.

In some embodiments, the directing the airflow to the one or more heat sinks of the microfluidic device may comprise directing the airflow in a substantially horizontal direction across the one or more heat sinks of the microfluidic device that has been inserted into the compartment of the cooling manifold. In other embodiments, the directing the airflow to the one or more heat sinks of the microfluidic device may comprise directing the airflow to impinge downwardly on the one or more heat sinks of the microfluidic device that has been inserted into the compartment of the cooling manifold. The directing the airflow to impinge downwardly on the one or more heat sinks of the microfluidic device may comprise directing the airflow to impinge downwardly in a substantially vertical direction on the one or more heat sinks of the microfluidic device that has been inserted into the compartment.

In some embodiments, the outputting the heated airflow from the cooling manifold through the outlet opening may comprise outputting the airflow from the cooling manifold in a substantially horizontal direction. In some embodiments, the microfluidic device may have been primed with necessary fluids before insertion. The method may comprise using the microfluidic device to perform polymerase chain reaction and/or thermal melt analysis and/or DNA extraction.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements. Additionally, the left-most digit(s) of the reference number identifies the drawing in which the reference number first appears.

FIG. 6A depicts a transparent view of the split-level cooling manifold of FIG. 4 and illustrate inlet (i.e., top) and outlet (i.e., bottom) ducts thereof according to one embodiment.

FIG. 6B depicts airflow through the inlet and outlet ducts of FIG. 6A according to one embodiment.

DETAILED DESCRIPTION OF PREFERRED EMBODIMENTS

Embodiments of the systems and methods for effectively delivering air to a microfluidic device are described herein with reference to the figures.

Figure 1:
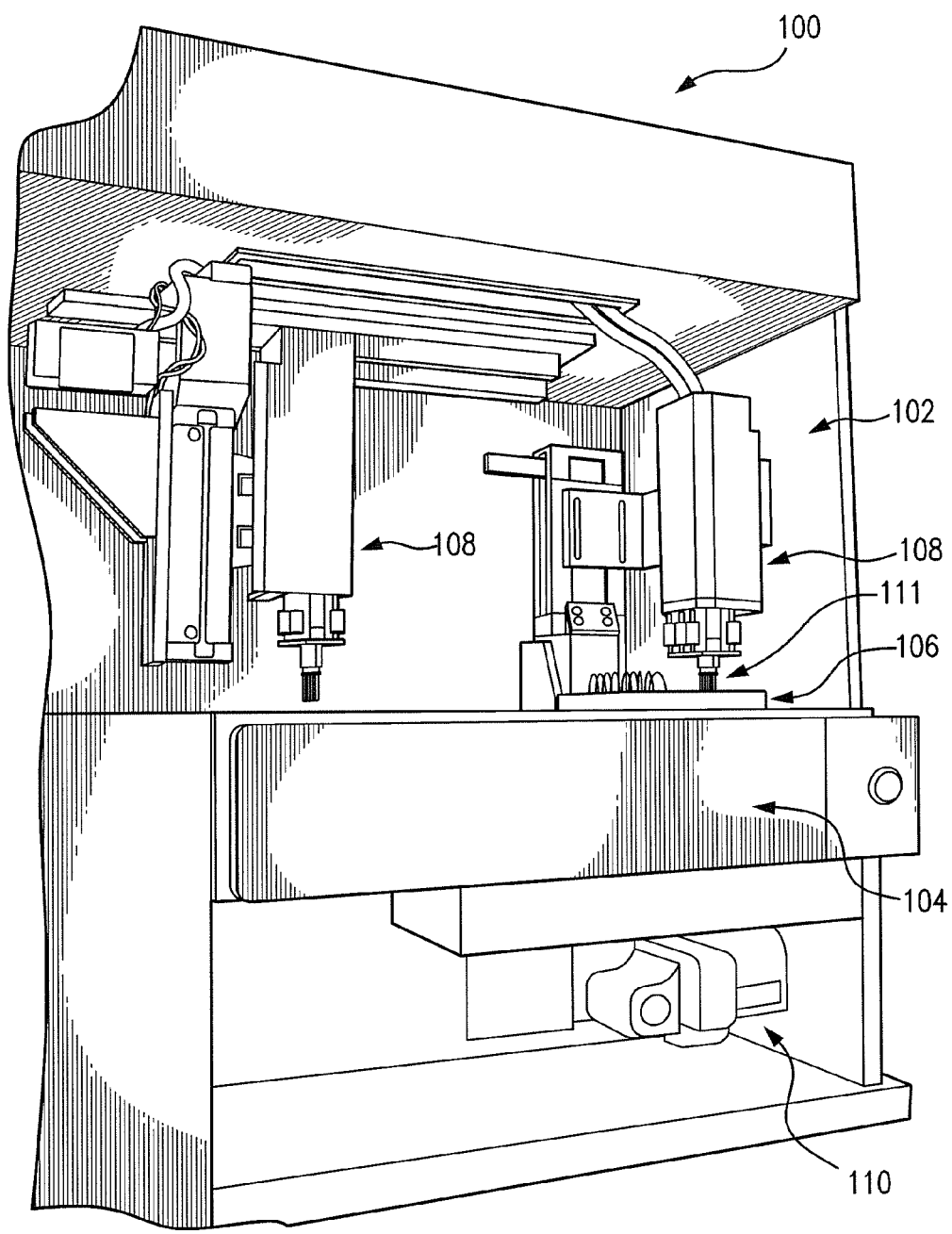
FIG. 1 depicts a front view of an instrument and illustrates several functional components thereof according to one embodiment.

FIG. 1 illustrates an instrument 100 according to one embodiment of the present invention. Instrument 100 may be a medical device. For example, instrument 100 may be a molecular diagnostic platform. In particular, instrument 100 may be a PCR and/or thermal melt system. However, instrument 100 may alternatively or additionally be a non-PCR instrument (e.g., an instrument that performs sample preparation and/or DNA extraction).

As shown in FIG. 1, instrument 100 has a frame 102, a drawer 104, a cooling manifold 106, a liquid handling system 108 and an optical system 110. In one embodiment, liquid handling system 108 may be robotic pipettors having pipette tips 111. Cooling manifold 106 may be located on a shelf of frame 102 above drawer 104. Optical system 110 may be located below drawer 104.

Figure 2:
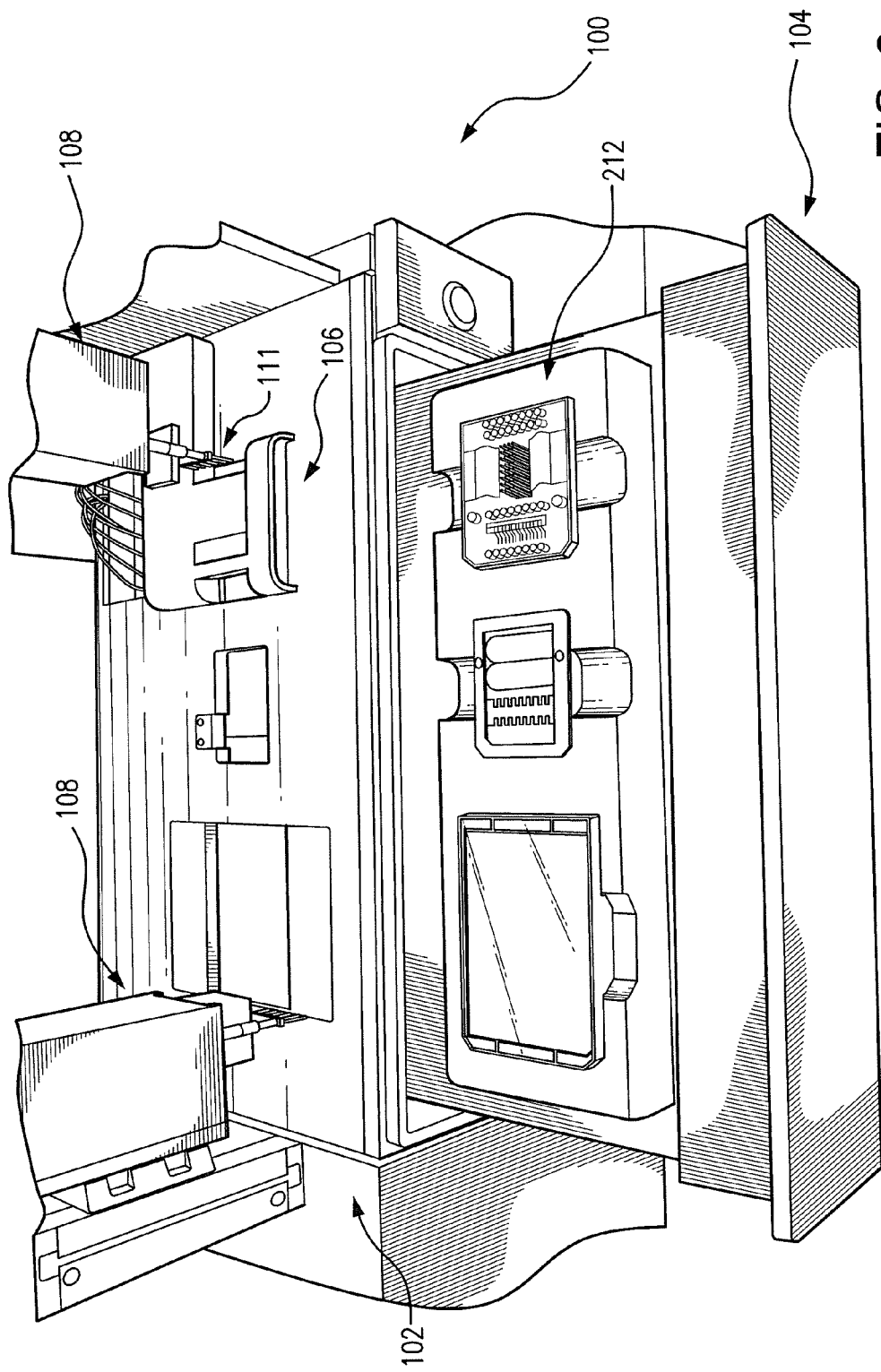
FIG. 2 depicts an elevated front view of the instrument shown in FIG. 1 with an open drawer according to one embodiment.
Figure 3A:
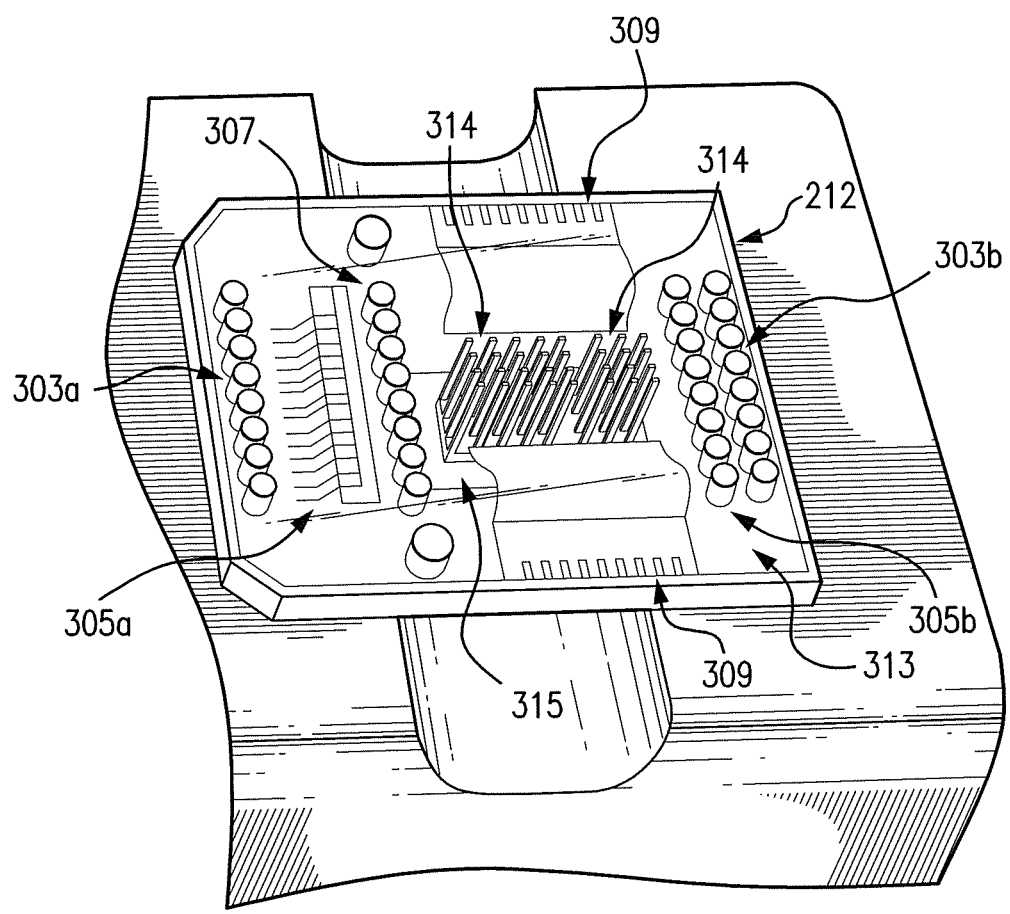
FIG. 3A depicts a microfluidic chip system of the instrument of FIG. 1 according to one embodiment.

As shown in FIG. 2, drawer 104 may contain a microfluidic chip system 212. In a non-limiting exemplary embodiment, the microfluidic chip system 212 includes an interface chip 313 and a microfluidic device (e.g., reaction chip) 315, as shown in FIG. 3A. In some embodiments, the interface chip 313 may contain storage wells (e.g., sample wells) 303a, pressure connection vent ports or wells 305a, inlet ports (e.g., access tubes or capillaries) 307, pressure connection waste ports or wells 305b, and/or storage wells (e.g., blanking wells) 303b. The inlet ports 307 may allow different fluids to be entered into the microfluidic device 315 in series. In one embodiment, microfluidic device 315 may be a device featuring at least one channel with at least one dimension that is less than 1 mm that may contain fluid (e.g., liquid or gas). Microfluidic device 315 may have many channels and may be multifunctional. Microfluidic device 315 may be capable of performing PCR and/or thermal melt analysis. Microfluidic device 315 may also be capable of performing DNA extraction. In some embodiments, the microfluidic chip system 212 may also have electrical connectors 309, which enable one or more electrical connections between the instrument 100 and the microfluidic chip system 212 to be made. Further, in some embodiments, the instrument 100 may contain a connector printed circuit board (PCB), and the electrical connectors 309 of the microfluidic chip system 212 may be configured to mate with corresponding electrical connectors of the connector PCB. Thus, the connector PCB may establish electrical connections between the instrument 100 and the microfluidic chip system 212.

In one embodiment, drawer 104, when open, may allow input of one or more disposables such as, for example, well plates, cleaning stations pipette tips and/or microfluidic devices. When the drawer 104 is closed, cooling manifold 106 may be located directly above microfluidic chip system 212, and optical system 110 may be located directly below the microfluidic chip system 212. In this exemplary embodiment, cooling manifold 106 provides a cooling airflow to microfluidic device 315 of microfluidic chip system 212. Optical system 110 may emit light to and receive light, possibly including fluorescent light, from microfluidic device 315. Optical system 110 may also be used to monitor the movement of fluid in microfluidic device 315. Examples of possible optical systems that may be used in the instrument 100 are described in U.S. Pat. No. 7,629,124, issued on Dec. 8, 2009, and in U.S. patent application Ser. No. 11/606,006, filed on Nov. 30, 2006, which are incorporated herein by reference in their entirety.

Figure 3B:
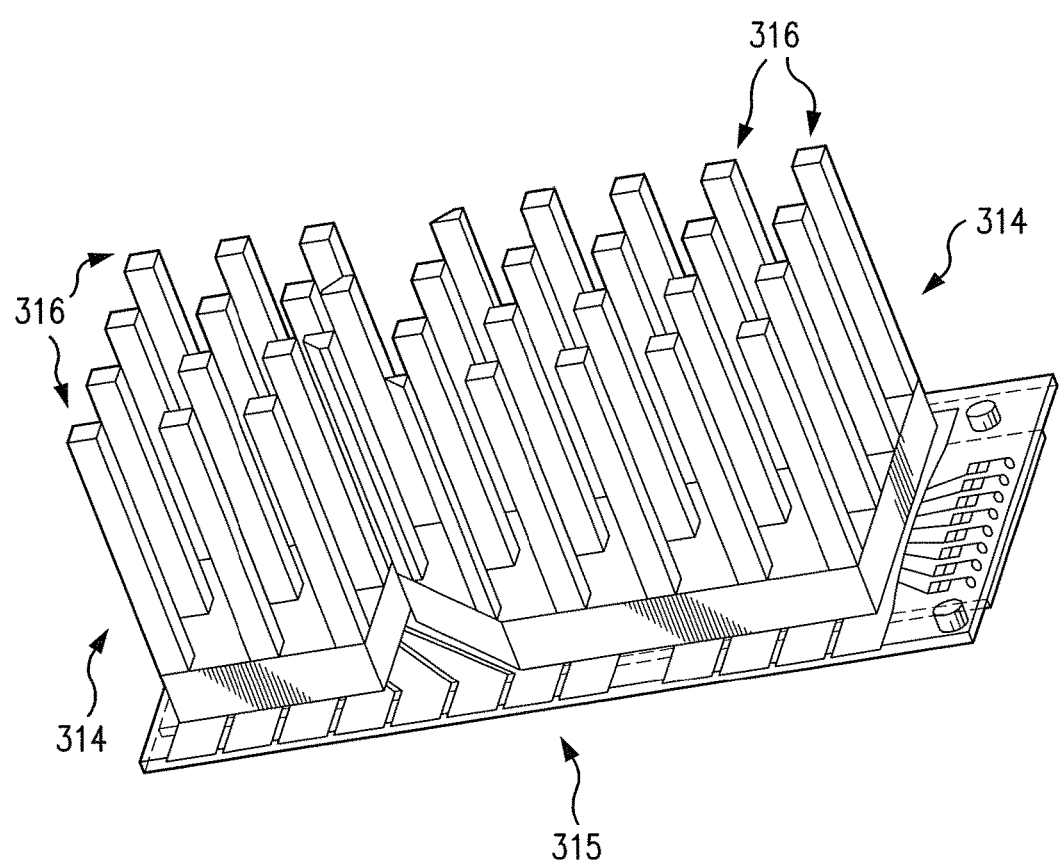
FIG. 3B depicts heat sinks of a microfluidic device of the microfluidic chip system of the instrument of FIG. 1 according to one embodiment.
Figure 3C:
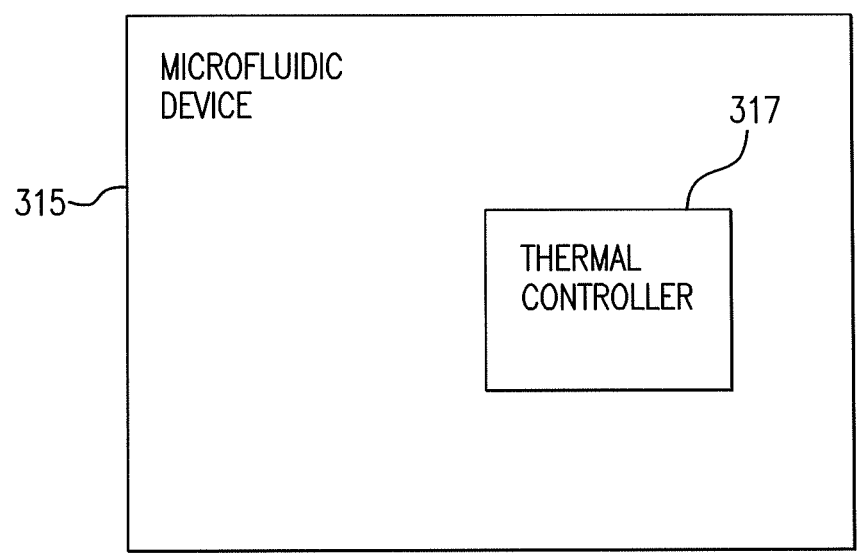
FIG. 3C is a block diagram illustrating a functional unit that may be part of a microfluidic device of the microfluidic chip system according to one embodiment.

FIGS. 3A-3C show an example of the manner in which microfluidic chip system 212 may be configured in accordance with one embodiment. Microfluidic device 315 of microfluidic chip system 212 may have a plurality of microfluidic channels extending across a substrate. Each channel may include one or more inlet ports and one or more outlet ports. Each channel may include a first portion extending through a PCR thermal zone and a second portion extending through a thermal melt zone. In some embodiments, a sipper can be used to draw liquid into the plurality of microfluidic channels. The microfluidic device 315 may include heater elements, which may be in the form of thin film resistive thermal detectors (RTDs). One or more heater elements may be associated with each microfluidic channel and may be located adjacent to the microfluidic channel.

Microfluidic device 315 may have one or more heat sinks 314. In one non-limiting embodiment, the heat sinks 314 may be bonded heat sinks. Other types of heat sinks may also be used, such as, for example, any of cast, extruded and folded fin heat sinks. In the illustrated embodiment, microfluidic device 315 has two heat sinks 314. One of the heat sinks 314 may be associated with at least one of a PCR thermal zone and a thermal melt zone of the microfluidic device 315, and another of the heat sinks 314 may be associated with at least the other of the PCR thermal zone and a thermal melt zone. In some embodiments, one heat sink or more than two heat sinks may be used. In an exemplary embodiment, heat sinks 314 may be pin-fin heat sinks having fins 316 extending upwards from microfluidic device 315 in a substantially vertical direction. Other fin designs may also be used including straight, louvered or bent fins, for example.

As illustrated in FIG. 3C, the microfluidic device 315 may have a thermal controller 317, which may be used to control temperature dependent reactions on the microfluidic device 212. Although the thermal controller 317 is illustrated in FIG. 3C as part of the microfluidic device 315, this is not necessary. The thermal controller 317 may alternatively be located off of microfluidic device 315 as a component of the microfluidic chip system 212 and/or instrument 100 and communicate with the microfluidic device 315. An example of one possible thermal controller and one possible microfluidic device that may be used in instrument 100 is described in U.S. patent application Ser. No. 12/825,476, filed on Jun. 29, 2010, which is hereby incorporated by reference in its entirety. Also, a thermal controller 317 is not necessary, and, in alternative embodiments, microfluidic device 315 and instrument 100 may not have a thermal controller.

Figure 4:
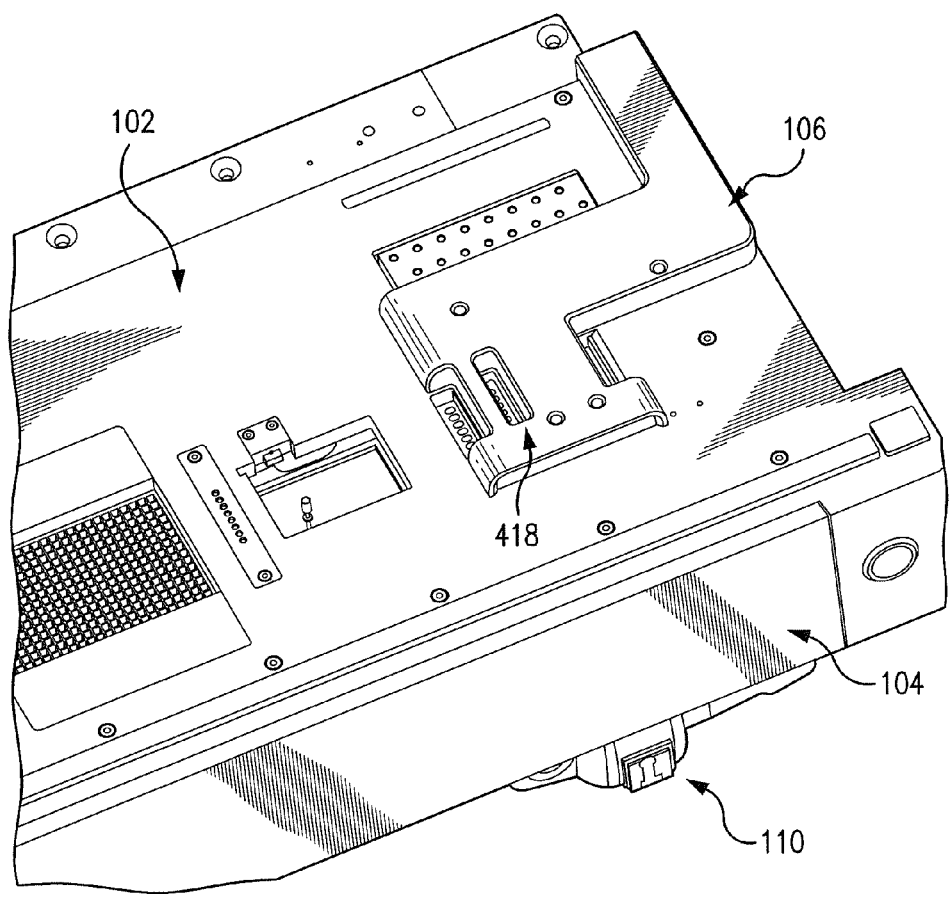
FIG. 4 depicts an elevated front view of the instrument of FIG. 1 and illustrates a split-level cooling manifold according to one embodiment.

FIG. 4 shows the cooling manifold 106 located above the microfluidic chip system 212 contained in drawer 104 in accordance with one embodiment. Cooling manifold may be configured to direct air to and/or from microfluidic device 315 of microfluidic chip system 212. Cooling manifold 106 may have a port 418 that allows chip-to-world fluid access or interface. As shown in FIG. 4, port 418 may be an opening extending through cooling manifold 106 to allow liquids to be delivered to the microfluidic device 315 without being disturbed by the cooling airflow. In other words, in some embodiments, the liquids may be exposed when being delivered to the one or more wells of microfluidic chip system 212 and/or one or more inlet ports of the microfluidic device 315 and/or in one or more sample wells of the microfluidic device 315 that store liquids on the microfluidic device 315, and the cooling manifold 106 isolates the cooling airflow from the exposed liquids at the inlet ports and/or sample wells and/or wells. Liquids can also be exposed at the one or more outlet ports. The cooling manifold 106 may, alternatively or in addition, isolate the cooling airflow from exposed liquids at the one or more outlet ports.

In some embodiments, one or more baffles are used to help keep cooling air directed at the heat sinks away from the exposed liquids. In one non-limiting embodiment, the baffles may be one or more gaskets added to the exterior of the cooling manifold 106. The gaskets may alternatively be added to the microfluidic device and/or microfluidic chip system instead of being added to the cooling manifold. The gaskets may be made of rubber but may alternatively be made from any suitable material, such as foam. In one embodiment, the one or more gaskets may include a rectangular gasket that fits outside the heat sink portion of the microfluidic device, keeps air in. The one or more gaskets may additionally or alternatively include one or more gaskets around fluid wells and inlet ports that keep air out.

In one embodiment, cooling manifold 106 may utilize a split level design such that inlet and outlet air streams are segregated into different ducts within the manifold. This enables warm air that is heated by the microfluidic device 315 to be directed away from microfluidic device 315. For instance, the air heated by the microfluidic device 315 may be directed outside the instrument to isolate the airflow from liquids and prevent heat build-up within the instrument. In directing the heated air away from the microfluidic device 315, cooling manifold 106 may direct the heated air to a rear enclosure 1037 (see FIG. 10), which is isolated from the front of instrument 100 shown in FIG. 1.

Figure 5:
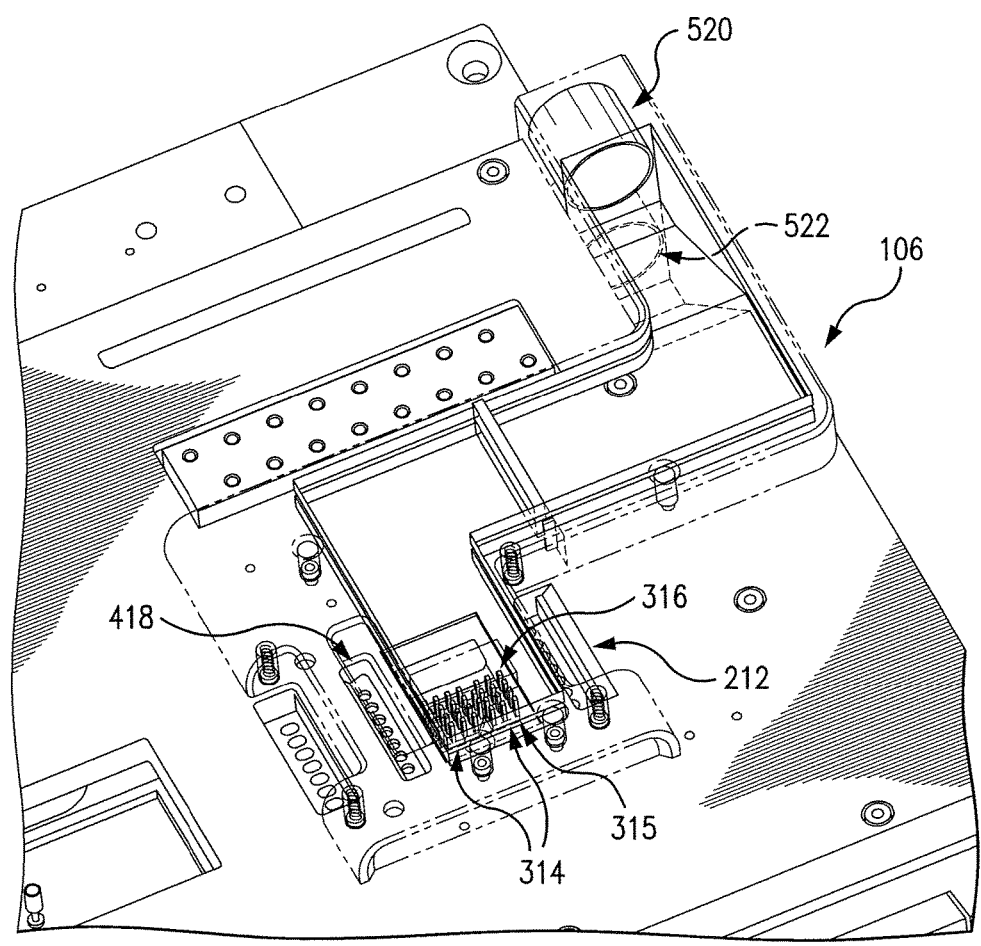
FIG. 5 depicts a transparent, elevated front view of the split-level cooling manifold of FIG. 4 when assembled in the instrument of FIG. 1 and illustrates the relationship of the split-level cooling manifold and microfluidic chip system according to one embodiment.
Figure 7A:
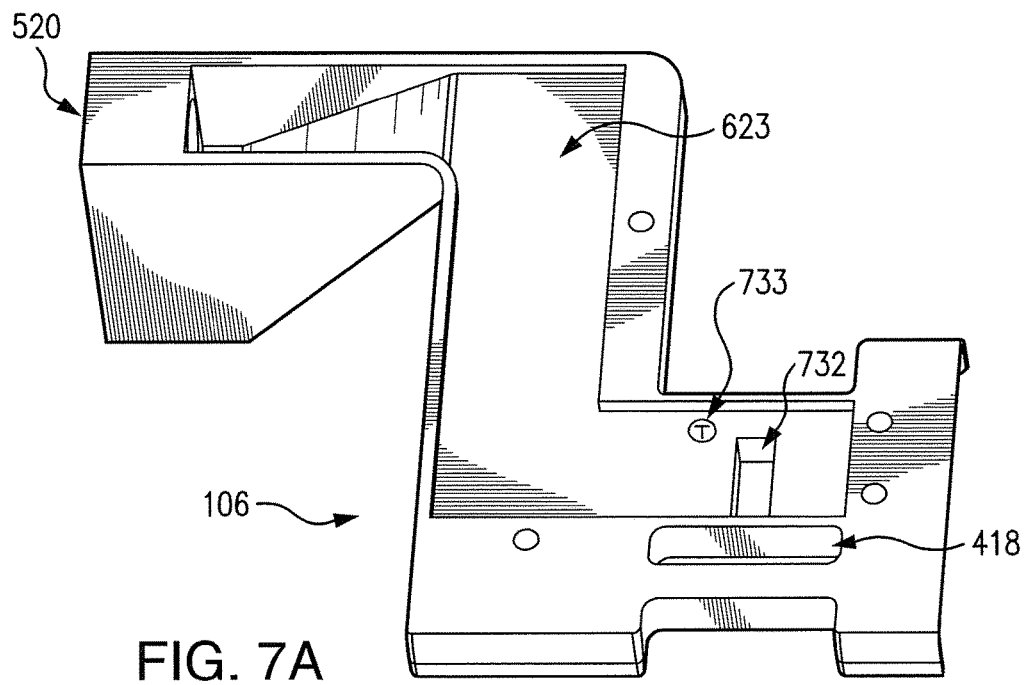
FIGS. 7A and 7B depict a cross-section view of the split-level cooling manifold of FIG. 4 illustrating the inlet duct according to one embodiment.
Figure 7B:
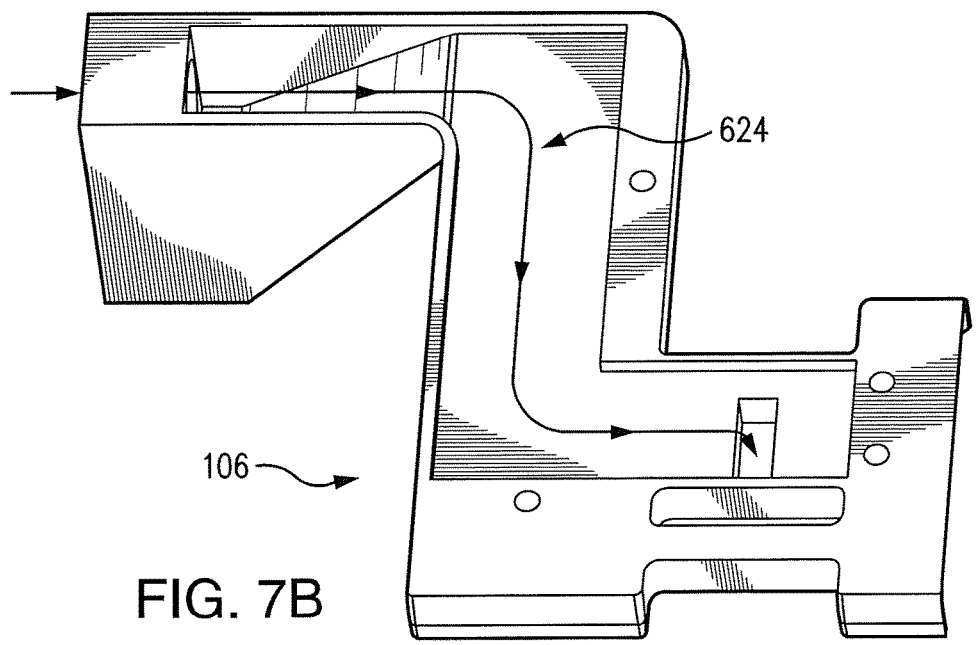
Figure 8A:
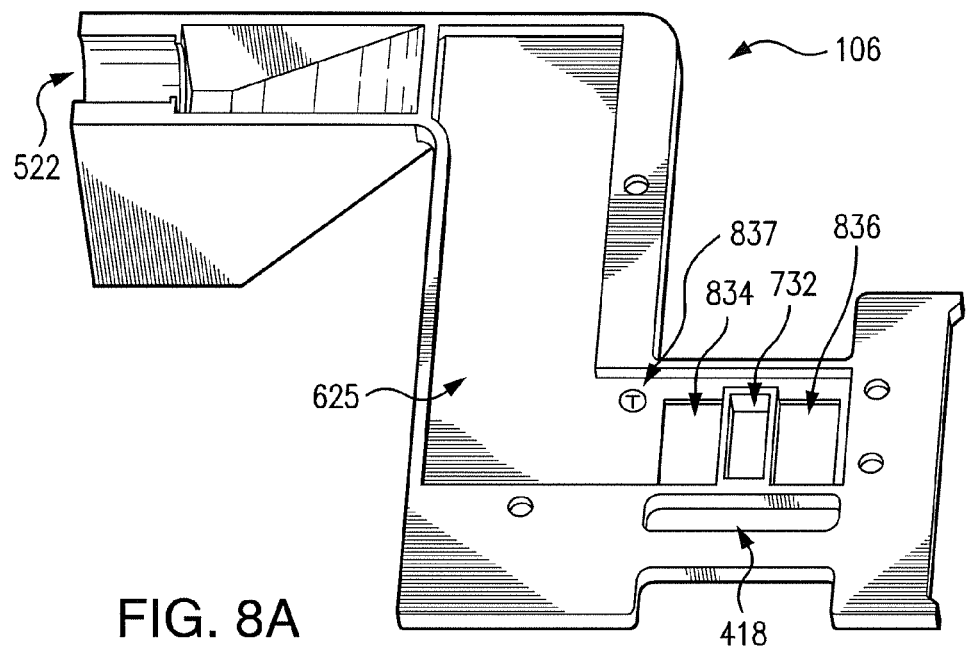
FIGS. 8A and 8B depict a cross-section view of the split-level cooling manifold of FIG. 4 illustrating the outlet duct according to one embodiment.
Figure 8B:
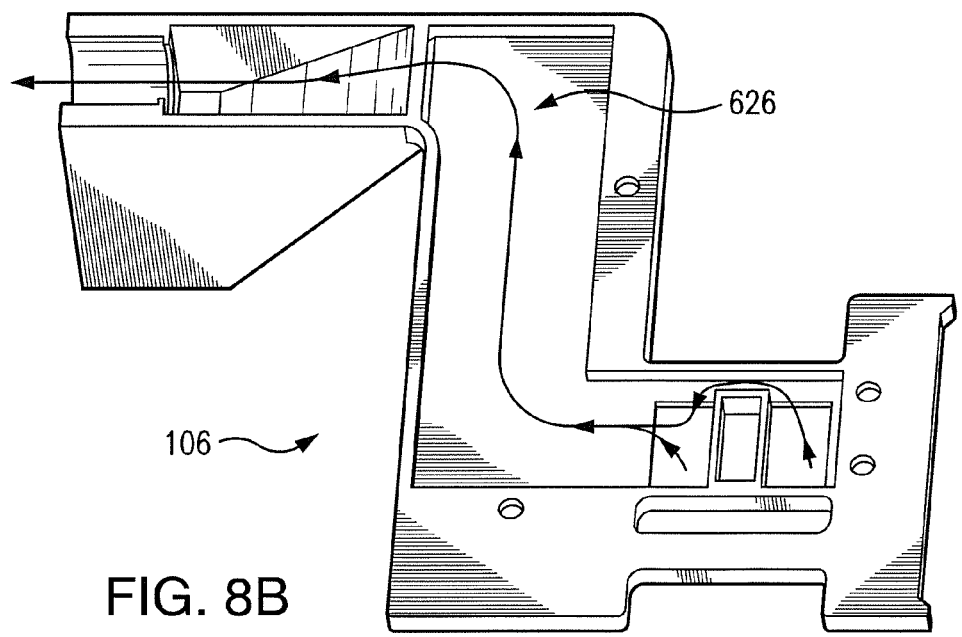
Figure 9A:
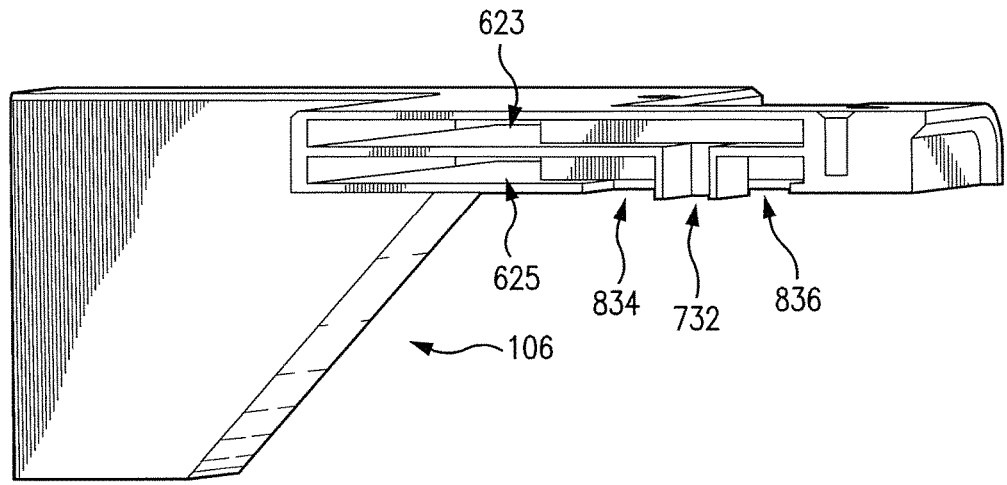
FIGS. 9A and 9B depict a side cross-section view of the split-level cooling manifold of FIG. 4 illustrating the inlet and outlet ducts and confinement channels according to one embodiment.
Figure 9B:
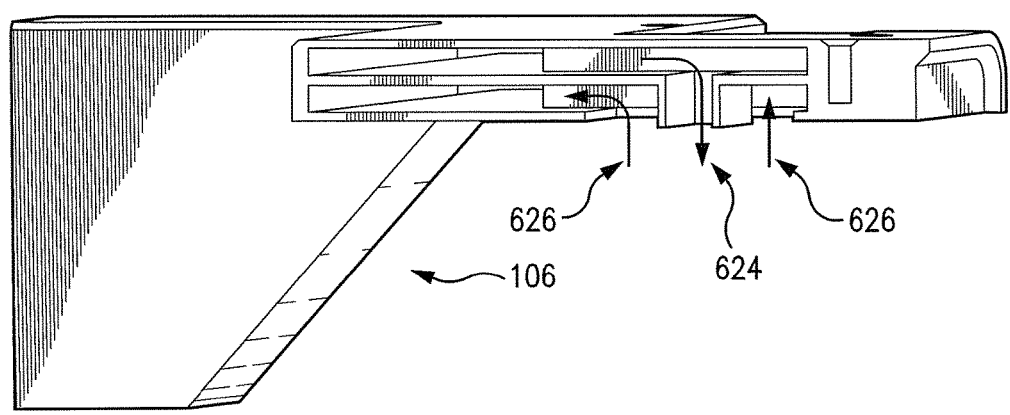

FIGS. 5, 6A, 6B, 7A, 7B, 8A, 8B, 9A and 9B illustrate the split levels of cooling manifold 106 according to one exemplary embodiment. FIG. 5 shows an inlet duct and an outlet duct of cooling manifold 106 when assembled in instrument 100 and shows the relationship of the cooling manifold 106 and microfluidic device 315 of microfluidic chip system 212. FIGS. 6A and 6B show inlet and outlet ducts of cooling manifold 106, their relationship to each other and the airflow of cooling air 624 and heated air 626 through the upper confinement channel 623 and lower confinement channel 625 respectively. FIGS. 7A and 7B depict a cross-section view of the split-level cooling manifold 106 to illustrate the upper, inlet duct and airflow of cooling air 624 in isolation. FIGS. 8A and 8B depict a cross-section view of the split-level cooling manifold 106 to illustrate the lower, outlet duct and airflow of the heated air 626 in isolation. FIGS. 9A and 9B depict a side cross-section view of the split-level cooling manifold 106.

In the illustrated embodiment, the top level forms an inlet duct and the bottom level forms an outlet duct. The inlet duct may comprise an inlet 520, upper confinement channel 623 and vertical channel 732. The outlet duct may comprise openings 834 and 836, lower confinement channel 625 and outlet 522. Cooling air 624 enters the inlet duct of cooling manifold 106 at inlet 520 and is directed towards vertical channel 732 through upper confinement channel 623. Cooling air 624 exits the inlet duct through vertical channel 732, which extends through the outlet duct, and is directed downwards onto the fins 316 of the one or more pin-fin heat sinks 314 of microfluidic device 315.

After being heated by the microfluidic device 315, heated air 626 enters the outlet duct of cooling manifold 106 through openings 834 and 836. Heated air 626 is then directed towards outlet 522 through lower confinement channel 625. Heated air 626 exits the outlet duct through outlet 522. As shown in FIG. 8B, heated air 626 that enters opening 836 at the front of cooling manifold 106 flows around vertical channel 732 on its path towards outlet 522.

In preferred embodiments, cooling manifold 106 does not significantly reduce the airflow rate and maintains a high heat transfer coefficient. Also, cooling manifold 106 may provide a substantially uniform airflow distribution to the device so that hot spots are not created on the device. For example, too little flow on the left side of the device 212, may cause overheating of that side of the device.

Although the upper level is used for the inlet duct and the lower level is used for the outlet duct in the illustrated embodiment, such a configuration is not required. In the alternative, the upper level may be used as an outlet duct and the lower level may be used as an inlet duct.

In some embodiments, one or more temperature measuring devices (i.e., temperature probes) may be located in the cooling manifold 106. The temperature measuring devices could be located anywhere along the manifold. In a preferred embodiment, the temperature measuring devices would be close to the heated microfluidic device so the measurement is indicative of the air temperature when it hits or flows off of the device. The temperature measuring devices may be, for example, wire like with a probe tip suspended in air. The wire may be supported by, for example, gluing or press-fitting the wire to the side of the manifold. Other temperature measuring device may be used, such as, for example, sensors in plastic or glass beads or other standard electronic packages (e.g., the DO-35 package). Also, in embodiments with a plurality of temperature measuring devices, the temperature measuring devices may all be of the same types or of different types. The temperature measuring device may be any suitable device known in the art for measuring temperature. The temperature measuring device may be, for example, a thermistor, thermocouple or resistance temperature detector.

In the illustrated embodiment, cooling manifold 106 may have a first temperature measuring device 733 located in the upper confinement channel 623. First temperature measuring device 733 may be located close to the microfluidic device 315 by the locating the first temperature measuring device 733 near the vertical channel 732. In an alternative embodiment, the first temperature measuring device 733 may be located in the vertical channel 732. For instance, the first temperature measuring device 733 may be located in the vertical channel 732 where cooling air 624 exits the cooling manifold 106.

In the illustrated embodiment, cooling manifold 106 may have a second temperature measuring device 837 located in the lower confinement channel 625. Second temperature measuring device 837 may be located close to the microfluidic device 315 by the locating the second temperature measuring device 837 near opening 834 and/or opening 836. For instance, the second temperature measuring device 837 may be located in the lower confinement channel 625 where heated air 626 enters the cooling manifold 106.

Figure 10:
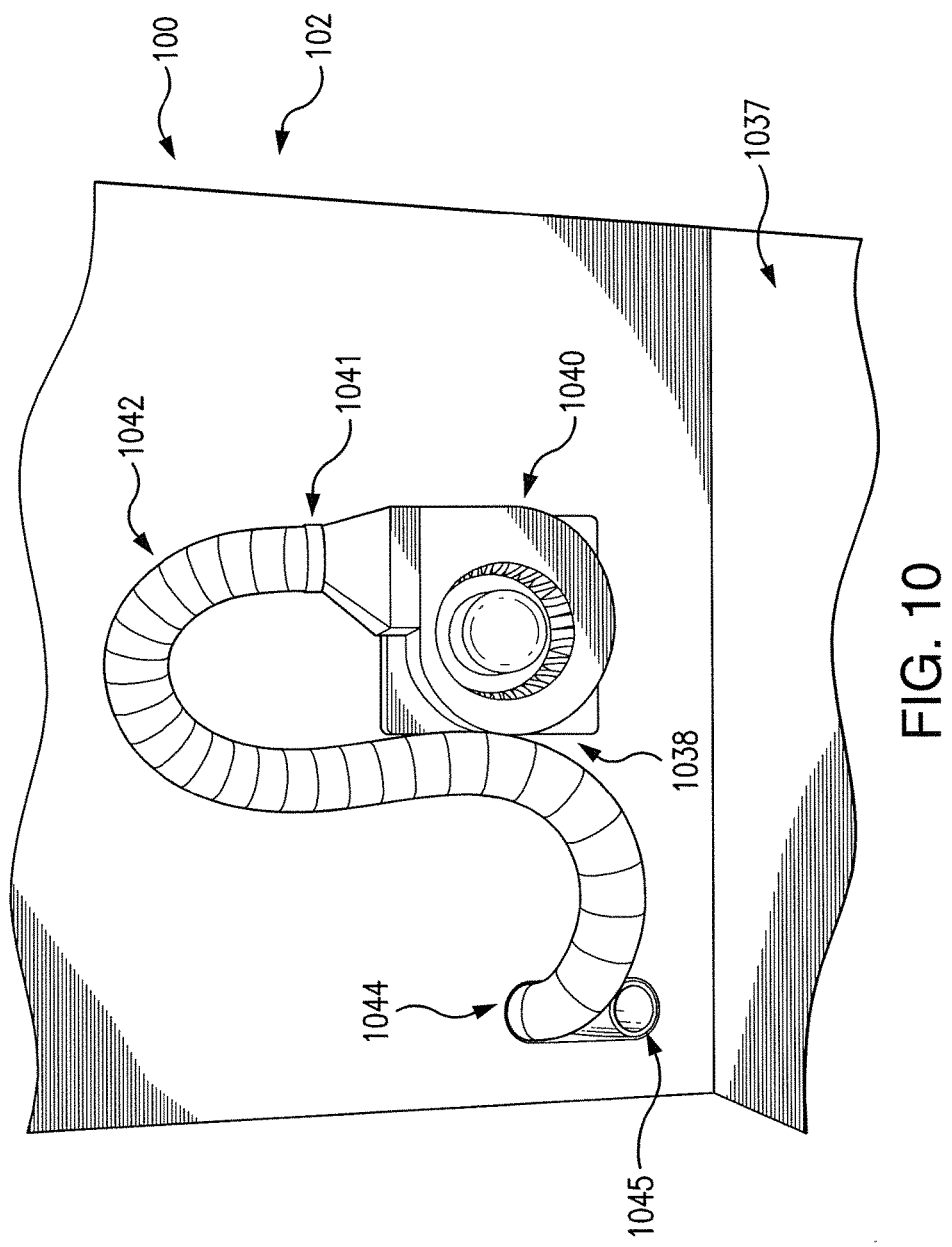
FIG. 10 depicts a rear view of the rear inside of the instrument of FIG. 1 and illustrates a blower, blower holder and duct according to one embodiment.

FIG. 10 depicts a rear enclosure 1037 of instrument 100 according to one embodiment. Rear enclosure 1037 may be enclosed and isolated from the front of instrument 100 shown in FIG. 1 by frame 102. Rear enclosure 1037 may contain a blower 1038. In a preferred embodiment, blower 1038 is a high pressure drop blower drive capable of high flow rates despite large pressure drops. In a non-limiting example, the San Ace B97 (9BMB12P2K01) made by Sanyo Denki may be used as blower 1038.

Blower 1038 may be attached to a wall of instrument 100 such that cool air may be drawn into the instrument 100. By doing so, a consistent stream of cool air is ensured irrespective of heat build-up inside instrument 100. Although the blower 1038 is shown as drawing air from rear enclosure 1037, blower 1038 may instead draw air from outside of instrument 100.

In one embodiment, blower 1038 may be supported and interfaced to a duct 1042 by a blower holder 1040. Blower holder 1040 directs the air flow from the outlet of blower 1038 into a duct mounting flange 1041. Duct 1042 may be connected from blower holder 1040 to inlet 520 of cooling manifold 106 through an opening 1044 in frame 102. Duct 1042 may be a flexible hose, such as corrugated tubing (e.g., Freelin Wade 1" corrugated tubing (1E-055-04)), or rigid pipes, for example, made of PVC.

Figure 11:
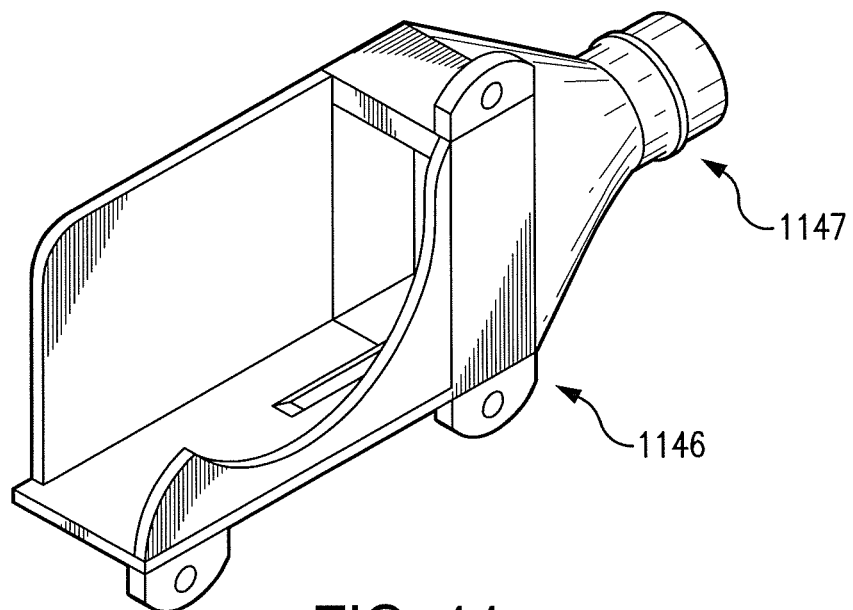
FIG. 11 depicts a blower holder according to one embodiment.
Figure 12:
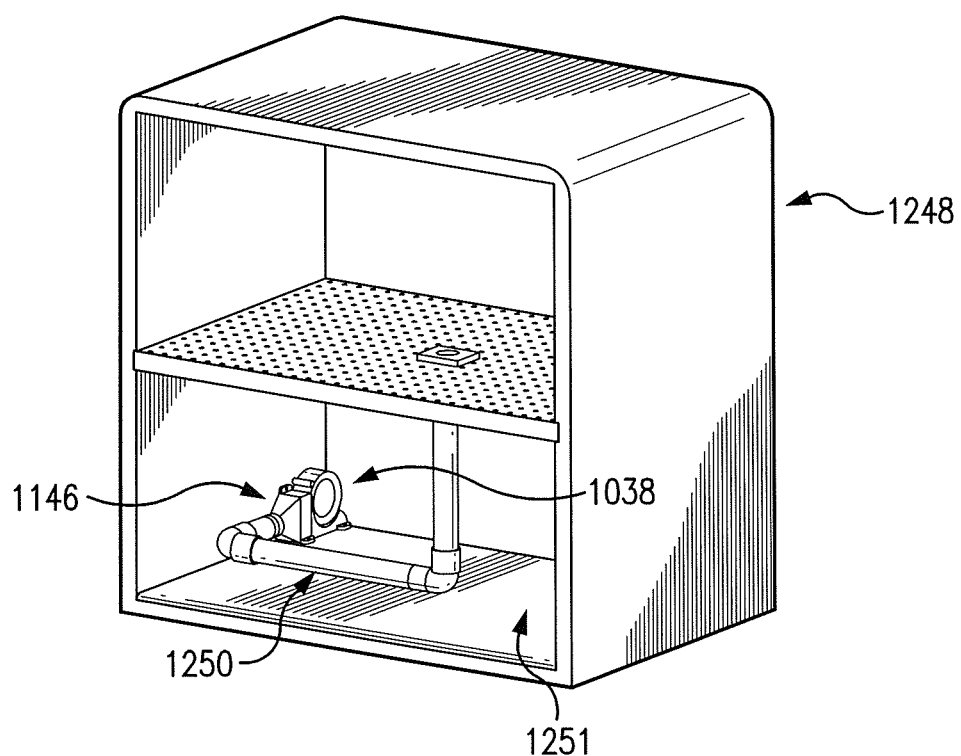
FIG. 12 depicts the blower holder of FIG. 11 mounted in an instrument, holding a blower and connected to a duct according to one embodiment.

FIGS. 11 and 12 illustrate a blower holder 1146 that could be used instead of the blower holder 1040 to support blower 1038 and interface blower 1038 to a duct 1250, in accordance with one embodiment. Blower holder 1146 is similar to blower holder 1040 and directs the air flow from the outlet of blower 1038 into a duct mounting flange 1147. Like duct 1042, duct 1250 may be connected from blower holder 1146 to inlet 520 of cooling manifold 106 through an opening 1044 in frame 102. Duct 1250 is shown as rigid pipes but may also be a flexible hose, such as, for example, corrugated tubing.

FIG. 12 also illustrates that the blower 1038 is not limited to being contained in a rear enclosure 1037 and could be located elsewhere. For example, blower 1038 could be contained in a lower enclosure 1251 of frame 1248.

In operation, airflow is ducted into instrument 100, and cooling manifold 106 directs the ducted airflow onto the microfluidic device 315. Cooling manifold 106 provides an effective cooling airflow that is isolated from exposed liquids. To isolate the airflow from exposed liquids, cooling manifold 106 directs the airflow away though a suitable outlet. Heated air may exit through an outlet within the instrument. For example, heated air 626 may simply exit outlet 522 into rear enclosure 1037 through opening 1045. In an alternative embodiment, heated air 626 may be further ducted away.

FIGS. 13A-13G illustrate a configuration of a cooling manifold in accordance with another embodiment of the present invention. Similar to cooling manifold 106, cooling manifold 1306 is a spit-level cooling manifold that ducts heated air away from a microfluidic device 315. However, in contrast to the vertical relationship of inlet 520 and outlet 522 of cooling manifold 106, inlet 1320 and outlet 1322 of cooling manifold 1306 have a horizontal relationship.

Figure 13A:
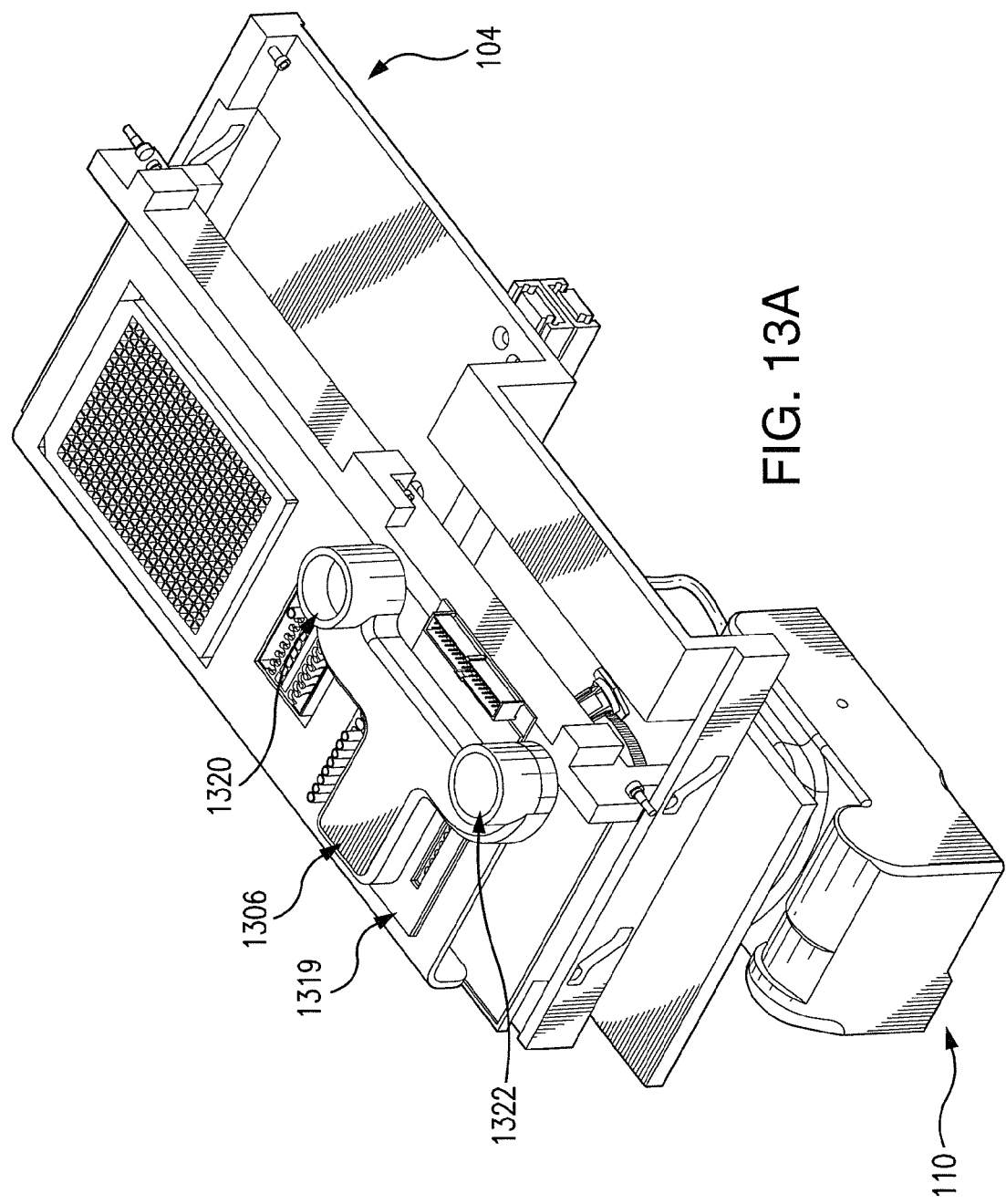
FIG. 13A depicts a cooling manifold and its positioning relative to other components of an instrument according to one embodiment.
Figure 13B:
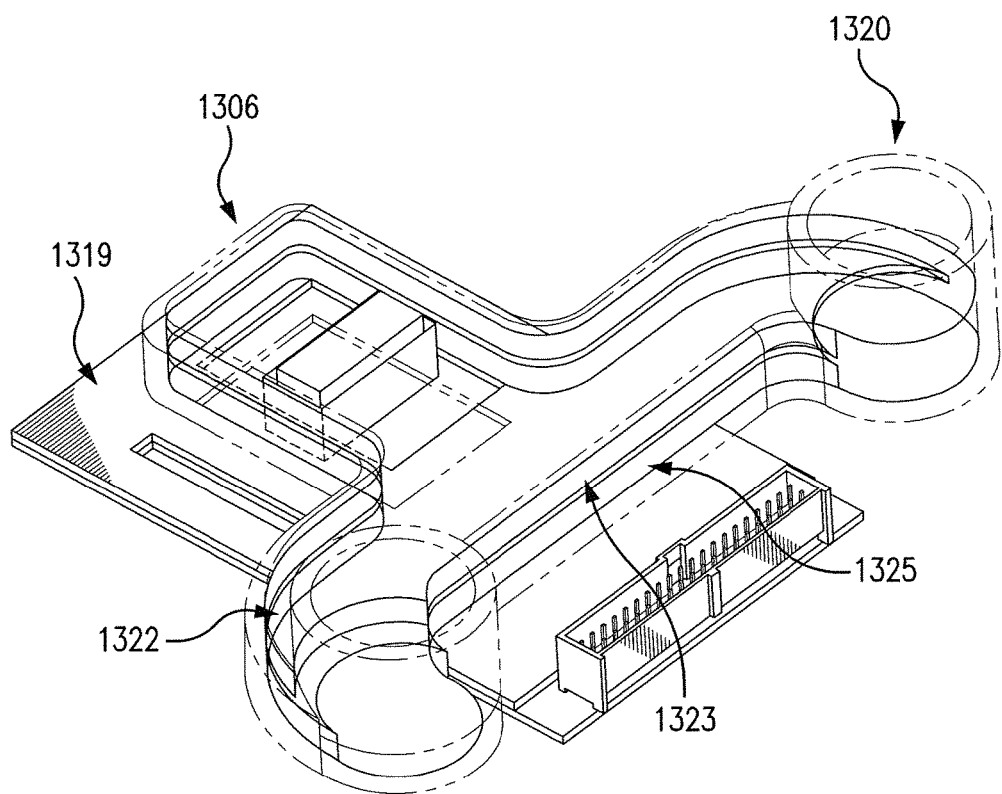
FIG. 13B depicts transparent view of the cooling manifold of FIG. 13A.
Figure 13C:
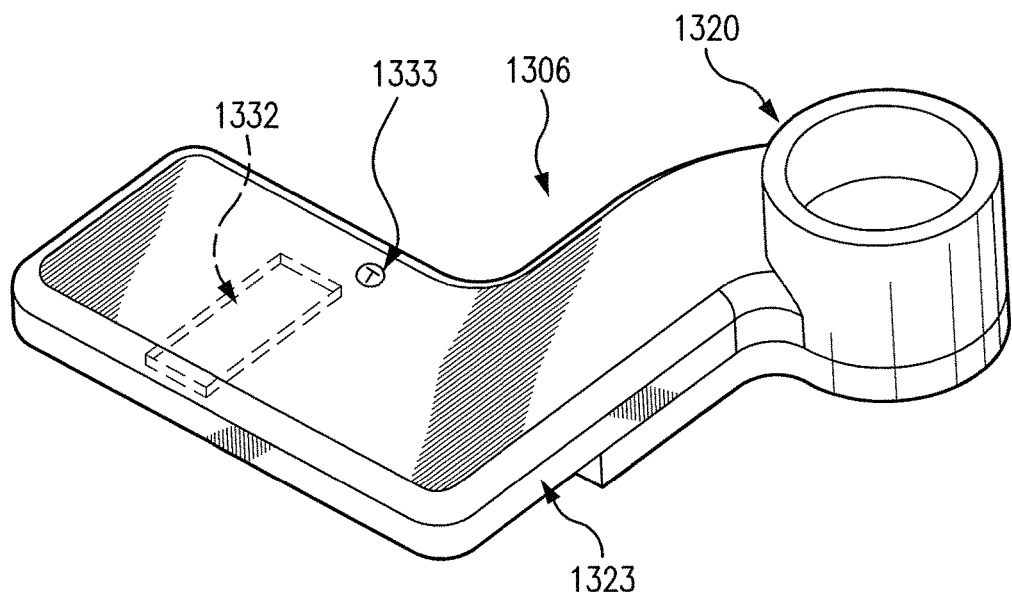
FIGS. 13C and 13D depict a transparent view of the inlet duct of the cooling manifold of FIG. 13A and airflow therethrough according to one embodiment.
Figure 13D:
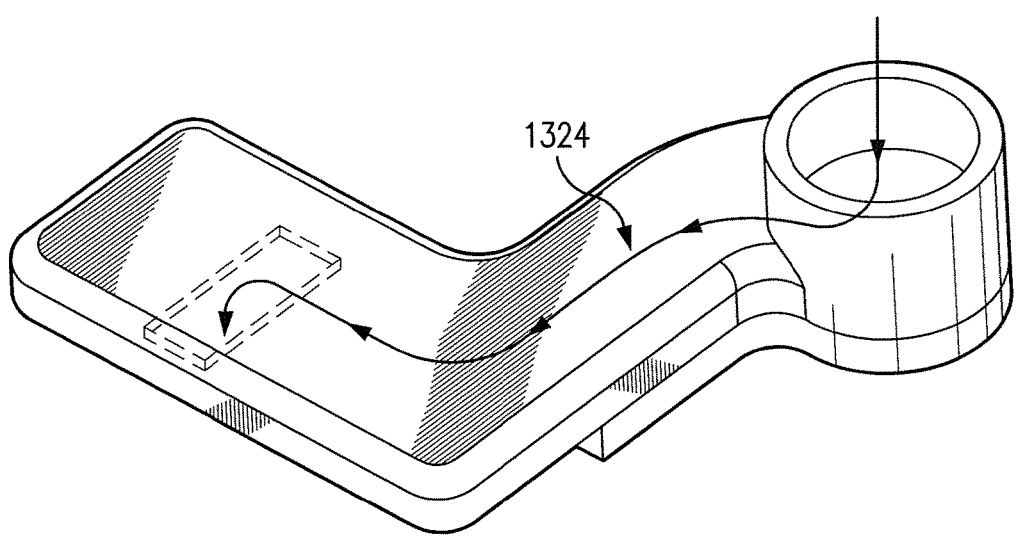
Figure 13E:
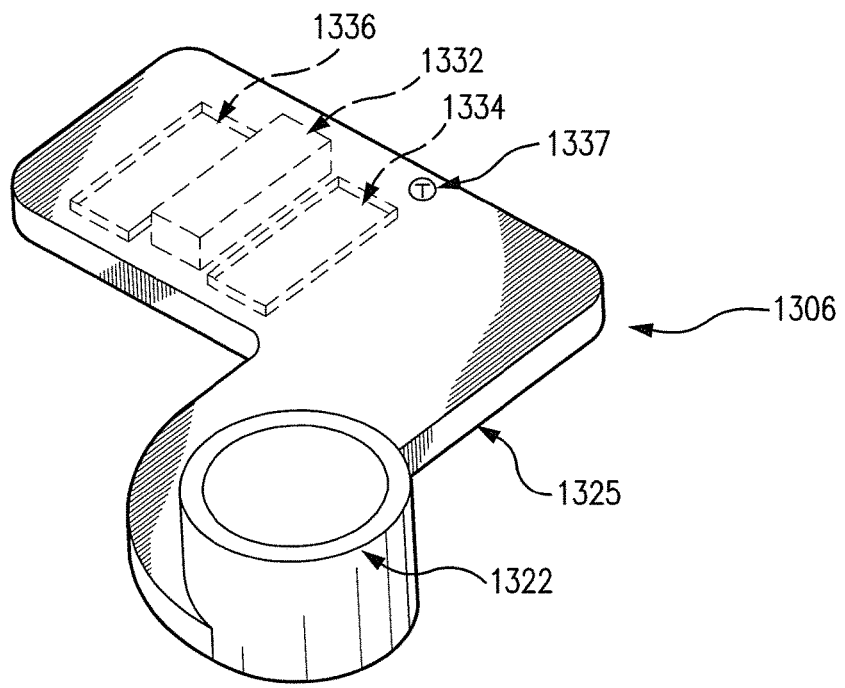
FIGS. 13E and 13F depict a transparent view of the outlet duct of the cooling manifold of FIG. 13A and airflow therethrough according to one embodiment.
Figure 13F:
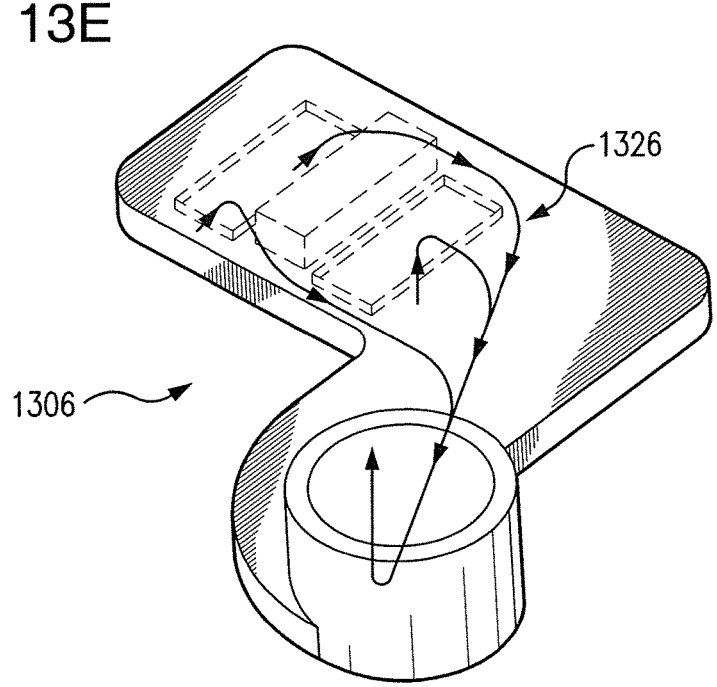
Figure 13G:
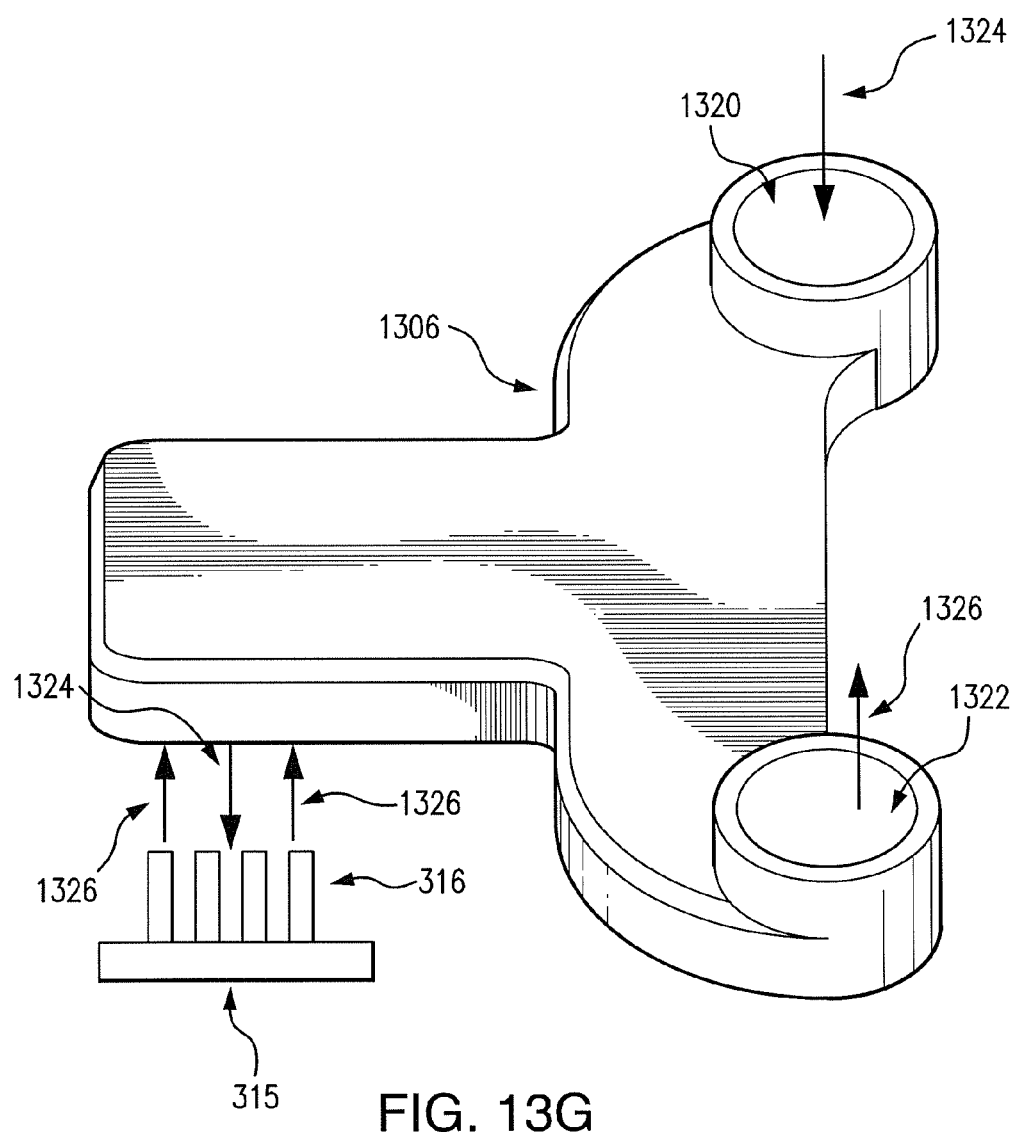
FIG. 13G depicts a side view of the cooling manifold of FIG. 13A and the transfer of cooling air and heated air between the cooling manifold and a microfluidic device according to one embodiment.

FIG. 13A shows cooling manifold 1306 and its positioning relative to a connector printed circuit board (PCB) 1319, drawer 104, and optical system 110 according to an embodiment of the invention. FIG. 13B illustrates the inlet and outlet ducts of cooling manifold 1306 and their relationship to connector PCB 1319. FIGS. 13C and 13D show the inlet duct of cooling manifold 1306 and the path of cooling air 1324. FIGS. 13E and 13F show the outlet duct of cooling manifold 1306 and the path of heated air 1326. FIG. 13G illustrates the transfer of cooling air 1324 and heated air 1326 between the cooling manifold 1306 and microfluidic device 315. The connector PCB 1319 may be a component of the instrument 100 and may be used to establish electrical connections between the instrument 100 and the microfluidic chip system 212. In FIG. 13A, the microfluidic chip system 212 is hidden underneath the connector PCB 1319.

In the illustrated embodiment, the top level forms an inlet duct and the bottom level forms an outlet duct. The inlet duct may comprise an inlet 1320, upper confinement channel 1323 and vertical channel 1332. The outlet duct may comprise openings 1334 and 1336, lower confinement channel 1325 and outlet 1322. Inlet 1320 is displaced in the horizontal direction relative to outlet 1322. Cooling air 1324 enters the inlet duct of cooling manifold 1306 at inlet 1320 and is directed towards vertical channel 1332 through upper confinement channel 1323. Cooling air 1324 exits the inlet duct through vertical channel 1332, which extends through the outlet duct, and is directed downwards onto the fins 316 of the one or more pin-fin heat sinks 314 of microfluidic device 315. As shown in FIG. 13G, in the illustrated embodiment, the microfluidic device 315 is positioned directly below the vertical channel 1332 of cooling manifold 1306. This position corresponds to the rectangular opening in connector PCB 1319 shown in FIG. 13B.

After being heated by the microfluidic device 315, heated air 1326 enters the outlet duct of cooling manifold 106 through openings 1334 and 1336. Heated air 1326 is then directed towards outlet 1322 through lower confinement channel 1325. Heated air 1326 exits the outlet duct through outlet 1322. As shown in FIG. 13F, heated air 1326 that enters opening 1336 at the front of cooling manifold 1306 flows around vertical channel 1332 on its path towards outlet 1322.

In some embodiments, one or more temperature measuring devices may be located in the cooling manifold 1306. The temperature measuring devices could be located anywhere along the manifold. In a preferred embodiment, the temperature measuring devices would be close to the heated microfluidic device so the measurement is indicative of the air temperature when it hits or flows off of the device.

In the illustrated embodiment, cooling manifold 1306 may have a first temperature measuring device 1333 located in the upper confinement channel 1323. First temperature measuring device 1333 may be located close to the microfluidic device 315 by the locating the first temperature measuring device 1333 near the vertical channel 1332. In an alternative embodiment, the first temperature measuring device 1333 may be located in the vertical channel 1332. For instance, the first temperature measuring device 1333 may be located in the vertical channel 1332 where cooling air 1324 exits the cooling manifold 1306.

In the illustrated embodiment, cooling manifold 1306 may have a second temperature measuring device 1337 located in the lower confinement channel 1325. Second temperature measuring device 1337 may be located close to the microfluidic device 315 by locating the second temperature measuring device 1337 near opening 1334 and/or opening 1336. For instance, the second temperature measuring device 837 may be located in the lower confinement channel 1325 where heated air 1336 enters the cooling manifold 1306.

Figure 19:
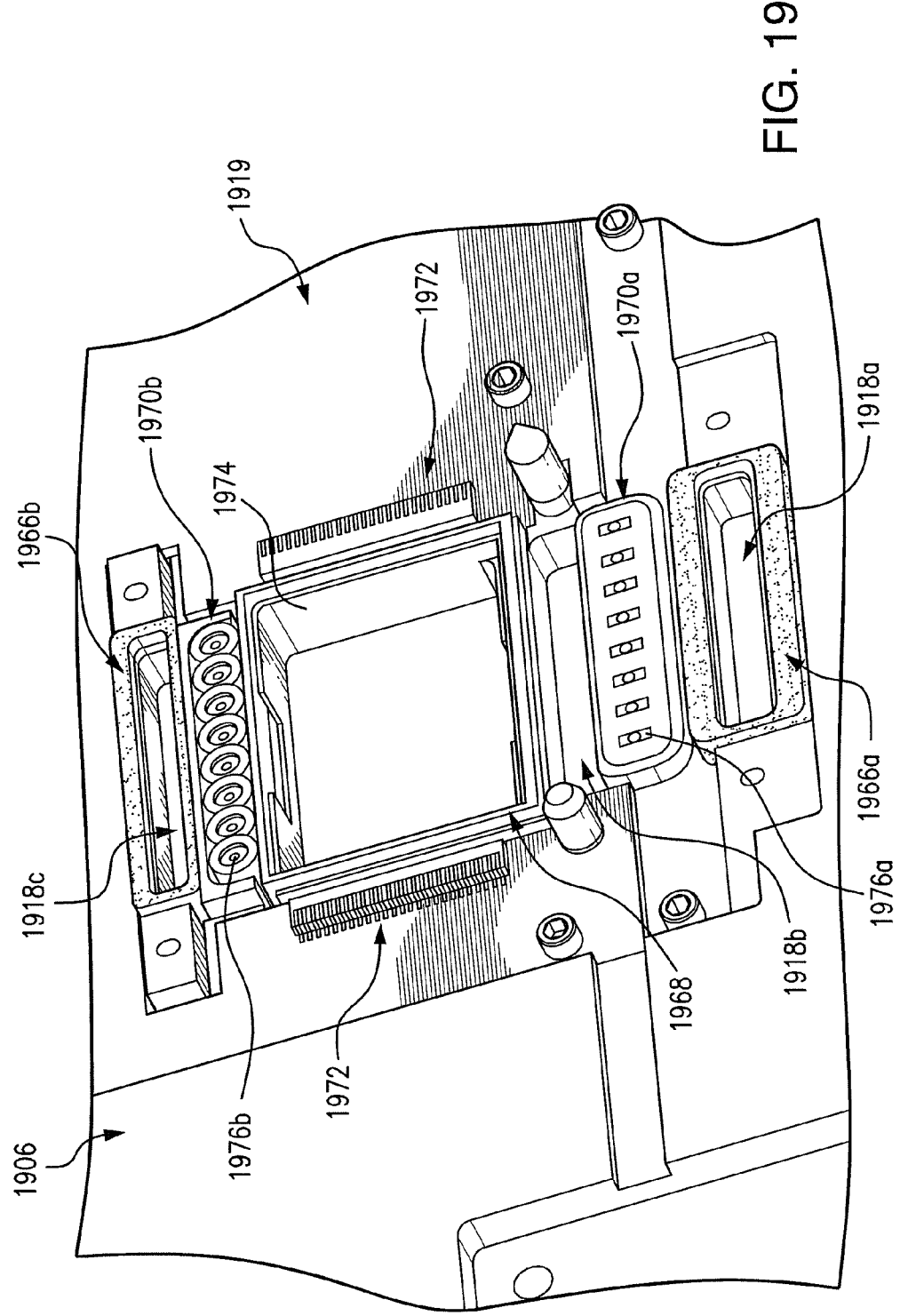
FIG. 19 depicts baffles of a microfluidic chip system of the instrument of FIG. 1 according to one embodiment.

As set forth above, in some embodiments, one or more baffles are used to help keep cooling air directed at the heat sinks away from the exposed liquids. In one non-limiting embodiment, the baffles may comprise one or more gaskets configured to provide an air-tight seal between portions of the microfluidic device 212 and the cooling manifold 1906 (which may correspond to manifold 106 or 1306). Such gasket(s) may be provided on the bottom of the cooling manifold 1906 wherein the manifold interfaces with the microfluidic device. Alternatively, gaskets may be provided on the microfluidic device itself and/or on portions of the shelf of the frame 102 above the drawer 104 that interface with portions of the microfluidic device 212. FIG. 19 shows a bottom portion of the cooling manifold 106 (1306) that extends through, or is aligned with, one or more openings formed in the shelf of the instrument frame 102 above the drawer 104. In other words, FIG. 19 is a view of the cooling manifold that might be seen looking up at the cooling manifold from inside drawer 104 of instrument 100.

In one embodiment, a connector printed circuit board ("PCB") 1919 is attached to the bottom of cooling manifold 1906. The connector PCB 1919 may include electrical contacts 1972, which may be configured to mate with and establish an electrical connection to electrical connectors (e.g., electrical connectors 309) of a microfluidic chip system (e.g., microfluidic chip system 212) when the microfluidic chip system is positioned beneath the manifold. The cooling manifold 1906 shown in FIG. 19 is configured to operatively mate with the microfluidic chip system 212 shown in FIG. 3A (although other manifold configurations for different microfluidic chip system configurations are contemplated) and includes access openings 1918a, 1918b and 1918c that extend through the cooling manifold 1906 and allow chip-to-world fluid access or interface (e.g., access for robotic pipettors having pipette tips 111 of instrument 100) to portions of the microfluidic chip system 212. Rectangular opening 1974 allows cooling air flowing within the manifold to flow to portions of the microfluidic chip system, such as the heat sinks 316, and allows heated air to flow from the microfluidic chip system back into the manifold to flow away from the microfluidic chip system. The manifold 1906 may also include pressure ports 1976a and pressure ports 1976b.

In the non-limiting embodiment shown in FIG. 19, the gaskets are configured to cooperate with a microfluidic chip system (e.g., microfluidic chip system 212) including a microfluidic device (e.g., microfluidic device 315) that will generally be aligned with rectangular opening 1974, one or more storage wells (e.g., sample wells 303a and/or blanking wells 303b) that will generally be aligned with access openings 1918a and 1918c, one or more inlet ports (e.g., inlet ports 307) that will generally be aligned with access opening 1918b, and pressure connection ports or wells (e.g., vent ports 305a and waste ports 305b) that will generally align with manifold pressure ports 1976a and 1976b. See, e.g., FIG. 3A. Access opening 1918a may provide access to sample wells (e.g., sample wells 303a) of the microfluidic chip system. Access opening 1918b may provide access to inlet ports (e.g., inlet ports 307) of the microfluidic device and may correspond to port 418 of cooling manifold 106. Access opening 1918c may provide access to blanking wells (e.g., blanking wells 303b) of the microfluidic chip system.

The gaskets may include well gaskets 1966a and 1966b that partially or completely surround access openings 1918a and 1918b, respectively, microfluidic device gasket 1968 that partially or completely surrounds rectangular opening 1974, and/or port gaskets 1970a and 1970b that surround the individual pressure ports 1976a and 1976b, respectively. Microfluidic device gasket 1968 surrounding the rectangular opening 1974 keeps in cooling air (e.g., cooling air 624, 1324) from the cooling manifold (e.g., cooling manifold 106 or 1306) and heated air (e.g., heated air 626, 1326) from one or more heat sinks of the microfluidic device. As shown in FIG. 19, microfluidic device gasket 1968 may be a rectangular gasket. However, the microfluidic device gasket 1968 may have rounded edges, and other shapes, such as an oval, may alternatively be used.

According to one embodiment, port gaskets 1970a and 1970b may be configured provide a substantially pressure tight seal between pressure ports 1976a and 1976b of the manifold 1906 and the vent ports 305a and waste ports 305b, respectively, so that pressure (positive pressure or vacuum) can be administered to the microfluidic chip system via the pneumatic coupling between the pressure ports 1976a and 1976b of the manifold 1906 and the vent ports 305a and waste ports 305b, respectively. In an embodiment, well gaskets 1966a and 1966b may be configured seal air (particularly the cooling air and heated air flowing in the manifold) out of the storage wells of the microfluidic chip system. In one embodiment, well gasket 1966a may be configured to seal air out of sample wells 303a of the microfluidic chip system, and well gasket 1966b may be configured to seal air out of blanking wells 303b of the microfluidic chip system. Some embodiments may include an additional well gasket surrounding port 1918b and configured to seal air out of the inlet ports of the microfluidic chip system. The additional well gasket may extend partially or completely around the inlet ports of the microfluidic chip system. The well gaskets 1966a and 1966b illustrated in FIG. 19 are configured to extend completely around the sample wells of the microfluidic chip system. However, this is not necessary, and, in alternative embodiments, well gaskets 1966a and/or 1966b may be configured to extend only partially around the sample wells of the microfluidic chip system.

In some embodiments, the well gaskets 1966a and 1966b and microfluidic device gasket 1968 may, individually and/or together, keep the cooling air from exposed liquids of the microfluidic chip system. Port gaskets 1970a and 1970b provide pressure tight seals with pressure ports 1976a and 1976b, respectively. However, in some embodiments, no baffles or gaskets are provided on the cooling manifold and/or microfluidic chip system. In one embodiment, the microfluidic device gasket 1968 alone is used to keep in cooling air from the cooling manifold and heated air from one or more heat sinks of the microfluidic device (and thereby keep the cooling air from exposed liquids of the microfluidic chip system), and the well gaskets 1966a and 1966b and/or port gaskets 1970a and 1970b are not provided.

In one embodiment, the drawer 104 includes angled guide tracks or other features that cause the drawer, and particularly the microfluidic chip system 212, to raise when the drawer 104 is closed. This will cause the microfluidic chip system 212 to be pressed against the gasket(s), thereby enhancing the sealing effects of the gaskets.

The gasket(s) may be made from any suitable gasket material, including silicone foam, neoprene.

Figure 14A:
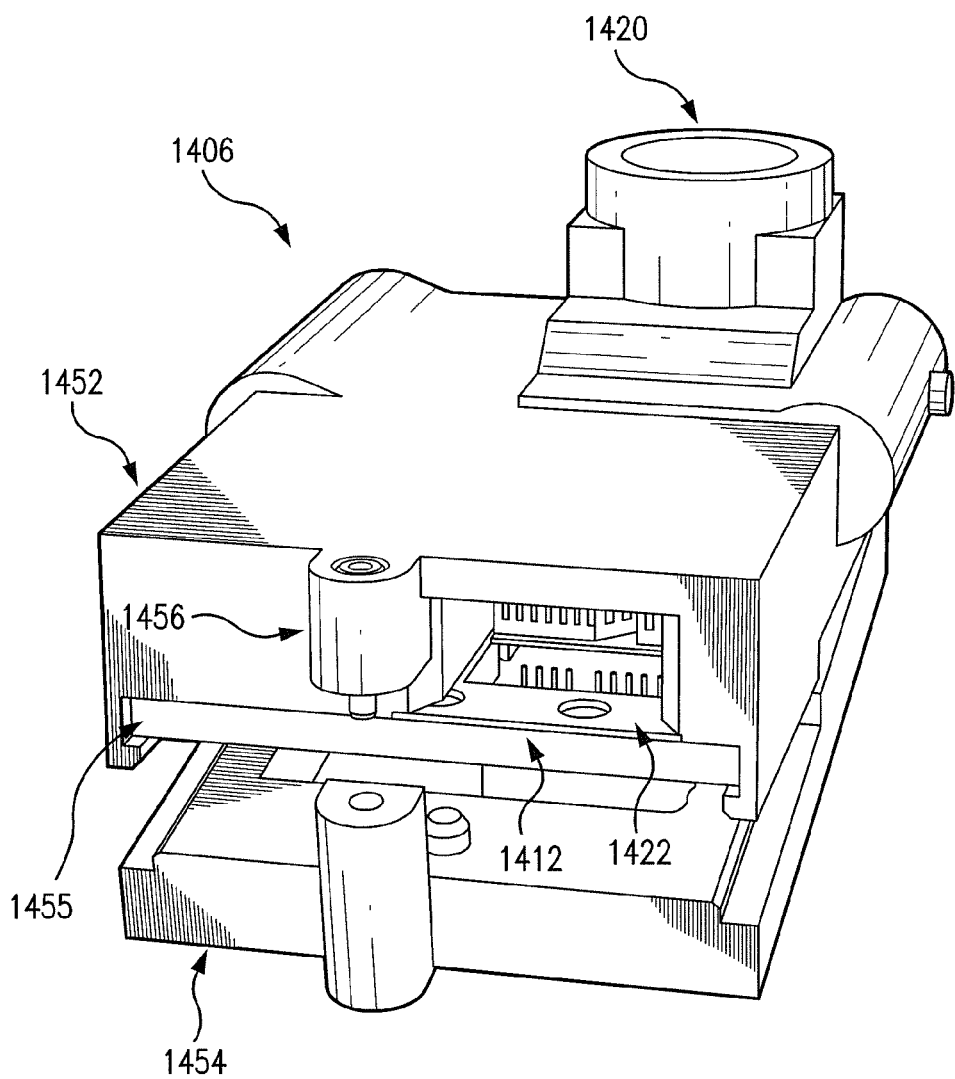
FIG. 14A depicts a front view of a clamshell cooling manifold for cross-flow across the microfluidic device according to one embodiment.
Figure 14B:
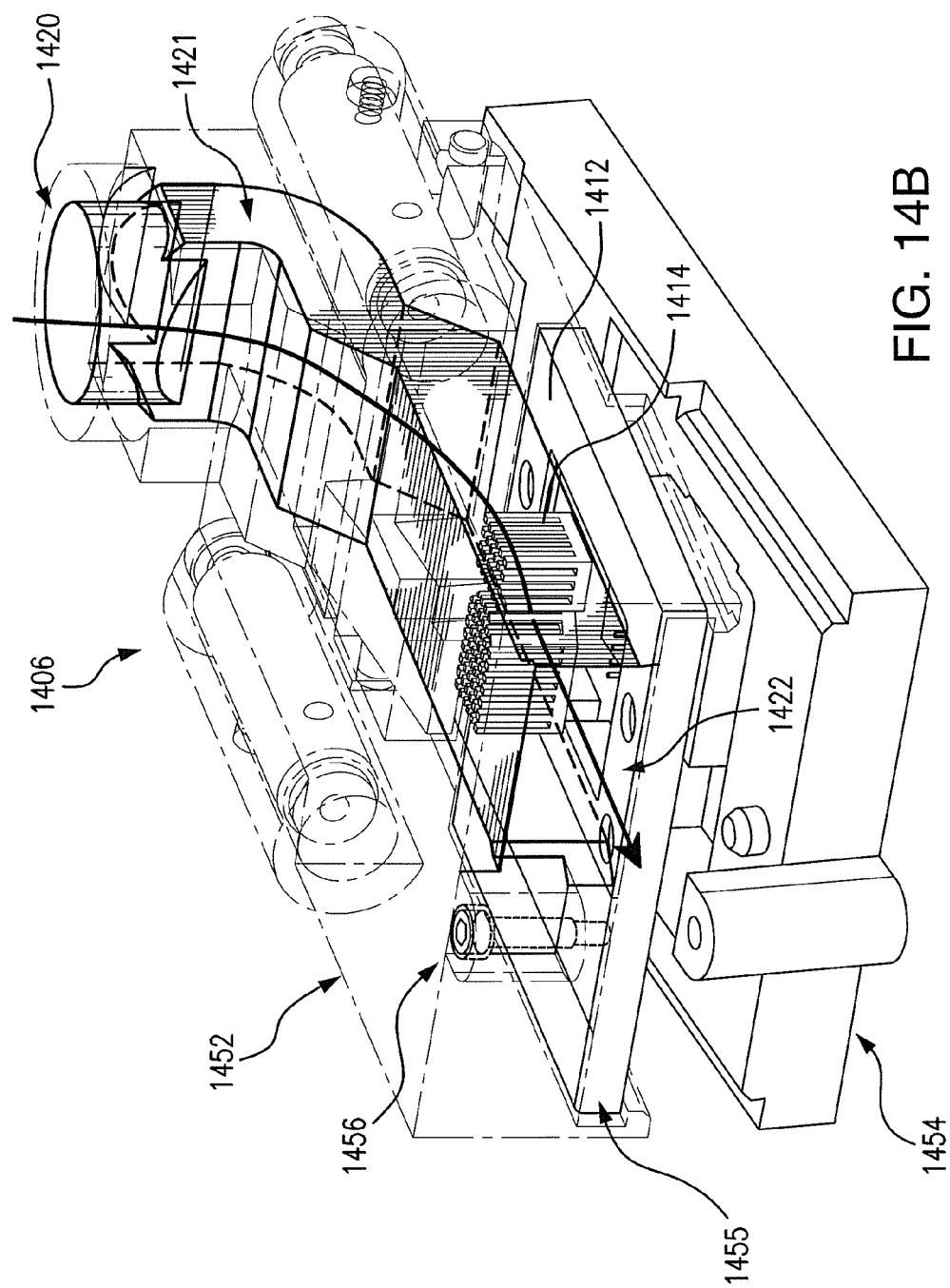
FIG. 14B depicts a transparent view of the cross-flow clamshell cooling manifold of FIG. 14A according to one embodiment.
Figure 14C:
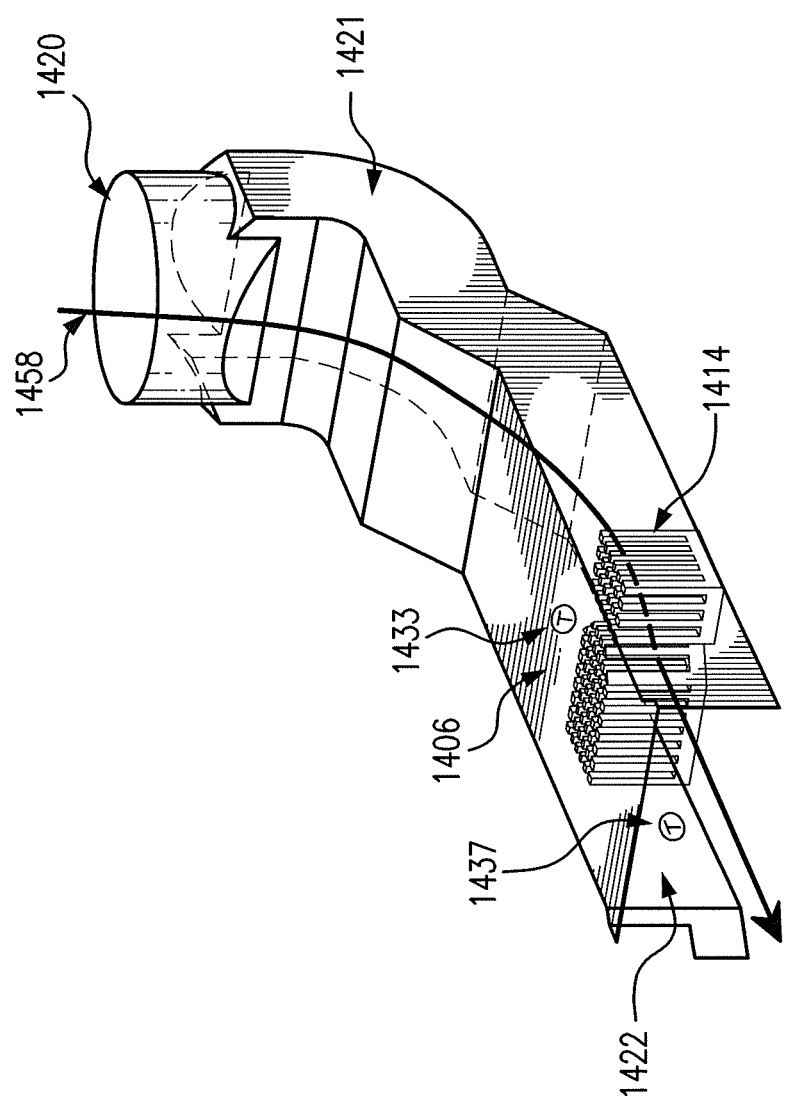
FIG. 14C depicts airflow through the cross-flow clamshell cooling manifold of FIG. 14A according to one embodiment.

Additional alternative configurations of the cooling manifold of the present invention are illustrated in FIGS. 14 and 15. The cooling manifolds of the embodiments illustrated in FIGS. 14 and 15 use a clamshell design that comprise a top piece and a bottom piece that can be fixed together. The clamshell design allows a microfluidic device 1412 (e.g., microfluidic cartridge) to be inserted and removed. Microfluidic device 1412 may be substantially similar to microfluidic device 315. In preferred embodiments, the microfluidic device 1412 is primed with necessary fluids before insertion into the clamshell cooling manifold. However, this is not required. In this embodiment, airflow comes into the top of the clamshell cooling manifold and is directed at the microfluidic device via an inlet duct (i.e., plenum, channel, or chamber), as shown in FIG. 14C. Because the microfluidic device 1412 is preferably primed with the desired fluids before the microfluidic device 1412 is inserted into the cooling manifold, the fluids are not exposed to the airflow. Instead, the fluids are isolated from the airflow by the microfluidic device 1412. However, in some embodiments, liquids may be exposed in the primed and inserted microfluidic device, and one or more baffles, such as, for example, the gaskets described above, may be added to the cooling manifold and/or to the microfluidic device and/or microfluidic chip system to isolate the exposed fluids from the airflow.

In one embodiment, the inlet duct may be formed in the top piece of the cooling manifold. The inlet duct is preferably circular or rectangular in cross-section. Other cross-section shapes also may be used. If the inlet duct has a rectangular cross-section, the rectangular inlet duct may uniformly distribute airflow to a substantially rectangular microfluidic device. If an input duct having a circular cross-section is attached to an inlet opening, the top piece of the cooling manifold preferably transforms the circular cross-sectional input duct into a rectangular inlet duct so that the airflow is uniformly distributed to the substantially rectangular microfluidic device. However, transforming a circular cross-section into a rectangular cross-section to accommodate a substantially rectangular microfluidic device is not necessary. Indeed, microfluidic devices and cooling manifolds having other shapes may be used as well.

In accordance with preferred embodiments, the clamshell cooling manifolds may utilize a cross-flow design or an impingement design. FIGS. 14A-14C illustrate a cross-flow clamshell cooling manifold 1406 according to one embodiment of the invention. FIG. 14A depicts a front view of clamshell cooling manifold 1406 for cross-flow across the microfluidic device 1412. FIG. 14B depicts a transparent view of the cross-flow clamshell cooling manifold 1406. FIG. 14C depicts airflow 1458 through the cross-flow clamshell cooling manifold 1406.

In the illustrated embodiment, cross-flow clamshell cooling manifold 1406 has a top piece 1452 and a bottom piece 1454 that can be fixed together by, for example, screw 1456. Top piece 1452 and bottom piece 1454 may be fixed together by other means such as, for example, press fitting, mechanical or magnetic latches, pneumatic compression or electromechanical actuation. Microfluidic device 1412 may be inserted and removed from a compartment 1455 in the clamshell cooling manifold 1406. The compartment 1455 may be formed in the top piece 1452, the bottom piece 1454 or both the top piece 1452 and the bottom piece 1454. In the illustrated embodiment, compartment 1455 is formed in top piece 1452.

As shown in FIG. 14C, cooling air 1458 enters cooling manifold 1406 at inlet opening 1420 and is directed at the microfluidic device 1412 via an inlet duct 1421, crosses over one or more heat sinks 1414 of microfluidic device 1412, and, after being heated by microfluidic device 1412, exits cooling manifold 1406 at outlet opening 1422. The inlet opening 1420, inlet duct 1421 and outlet opening 1422 may be part of (i.e., included in) the top piece 1442 of cooling manifold. However, in some embodiments, it is possible for any of the inlet opening 1420, inlet duct 1421 and/or outlet opening 1422 to be entirely or partially part of the bottom piece 1454.

In the illustrated embodiment, when the cooling air 1458 crosses over one or more heat sinks 1414 of microfluidic device 1412, the cooling air 1458 may cross over the one or more heat sinks 1414 of microfluidic device 1412 in a substantially horizontal direction. When the cooling air 1458 exits cooling manifold 1406 at outlet opening 1422, the cooling air 1458 may exit cooling manifold 1406 in a substantially horizontal direction.

In some embodiments, one or more temperature measuring devices may be located in the cooling manifold 1406. The temperature measuring devices could be located anywhere along the manifold. In a preferred embodiment, the temperature measuring devices would be close to the heated microfluidic device so the measurement is indicative of the air temperature when it hits or flows off of the device.

In the illustrated embodiment, cooling manifold 1406 may have a first temperature measuring device 1433 located in the inlet duct 1421. First temperature measuring device 1433 may be located close to the microfluidic device 1412. Cooling manifold 1406 may have a second temperature measuring device 1437 located near outlet 1422.

Figure 15A:
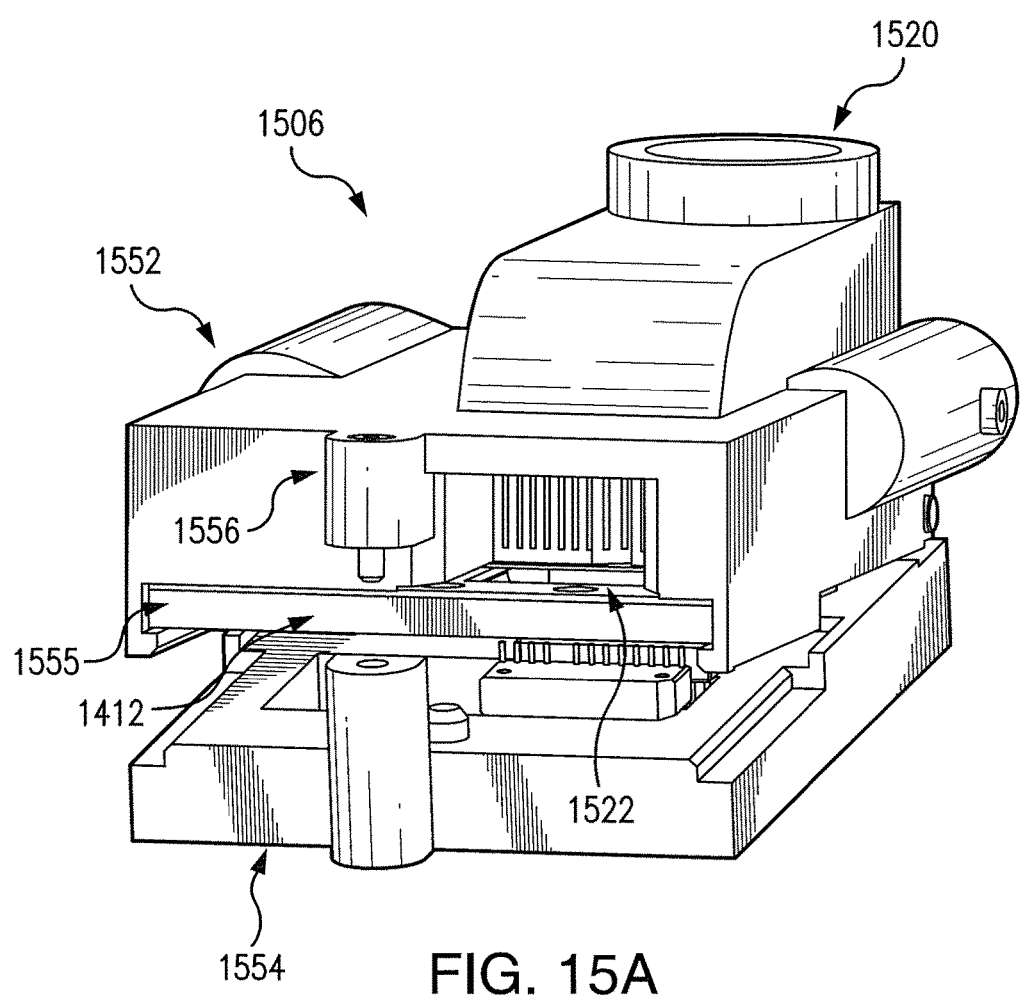
FIG. 15A depicts a front view of a clamshell cooling manifold for impingement cooling of the microfluidic device according to one embodiment.
Figure 15B:
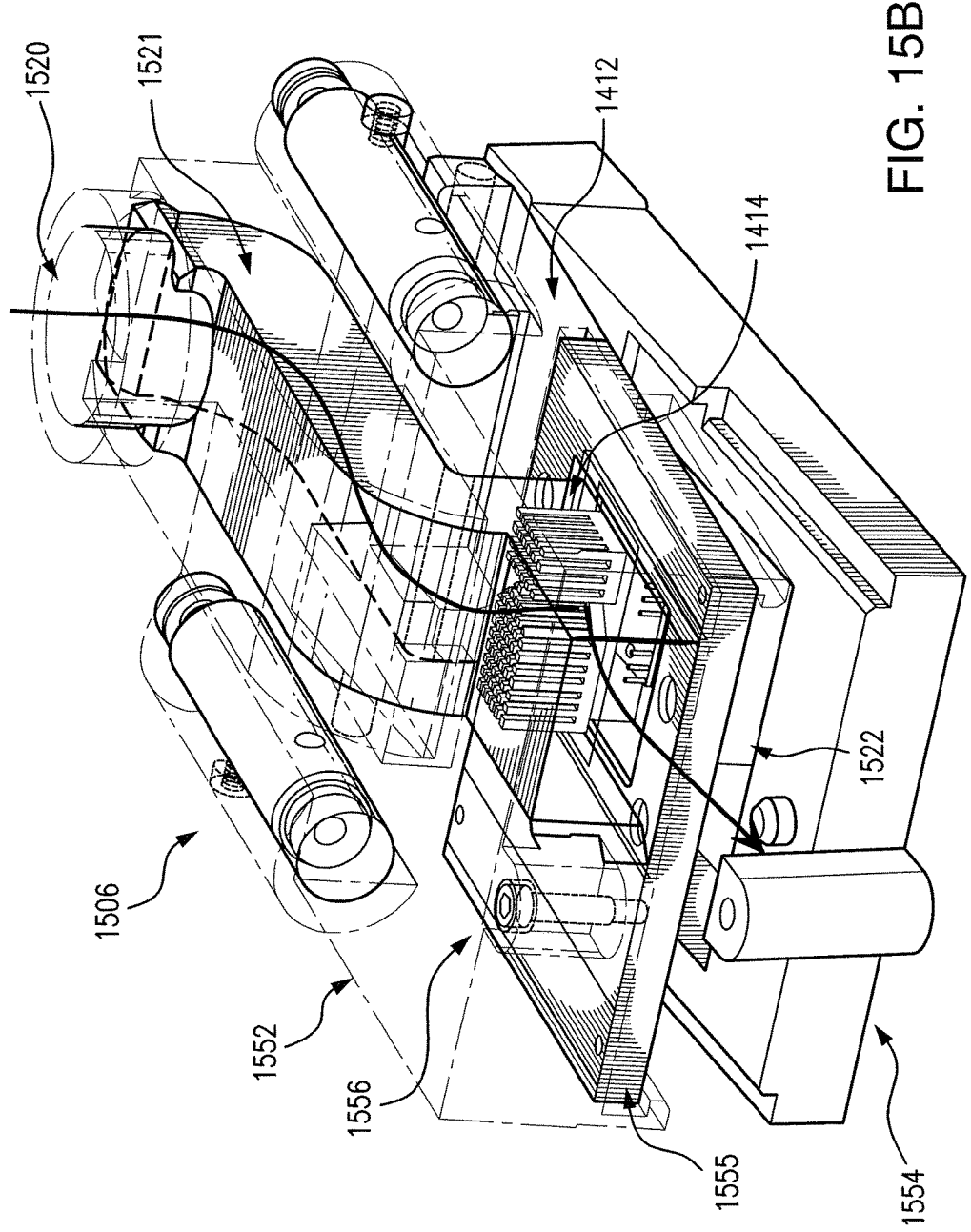
FIG. 15B depicts a transparent view of the impingement clamshell cooling manifold of FIG. 15A according to one embodiment.
Figure 15C:
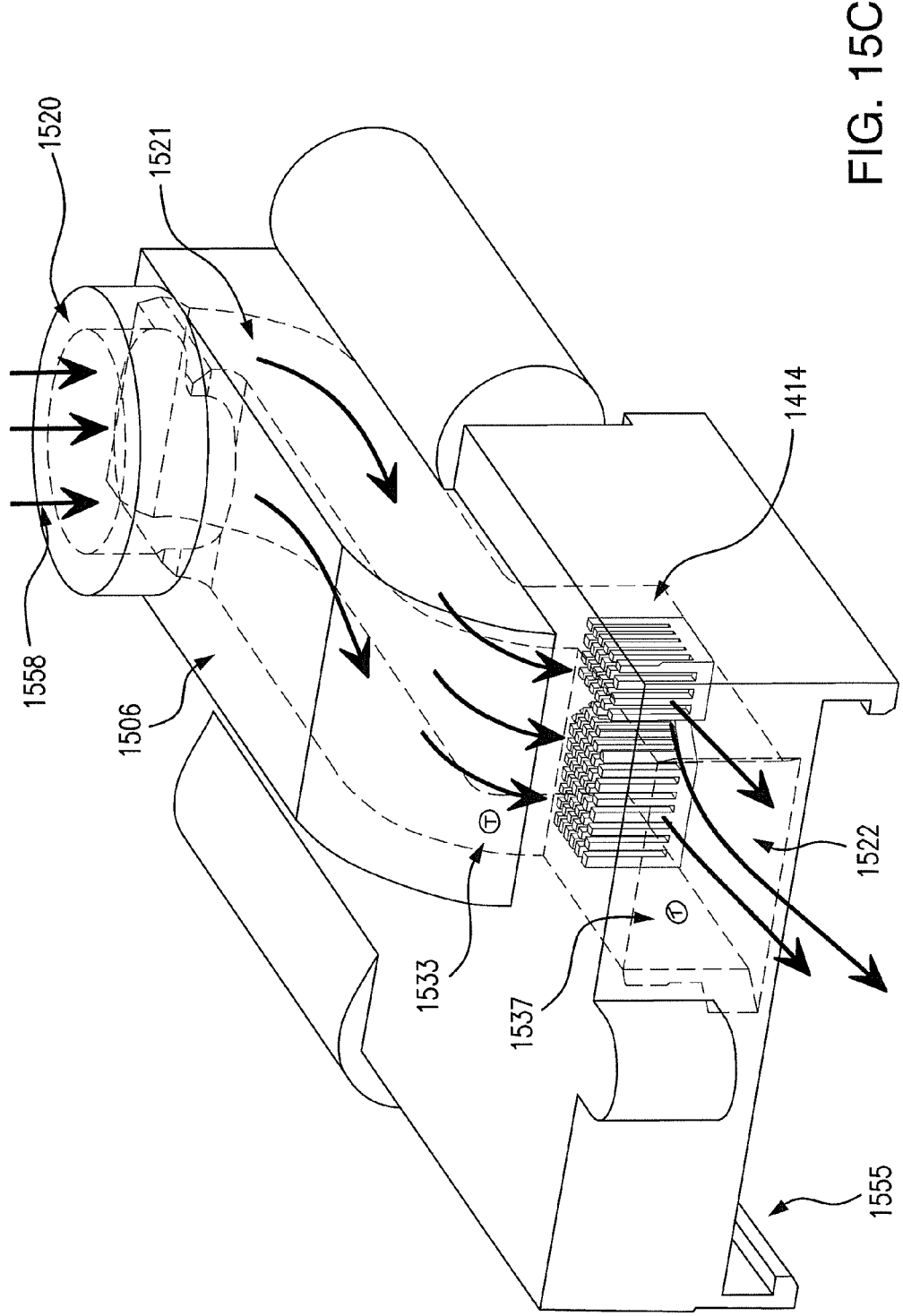
FIG. 15C depicts airflow through the impingement clamshell cooling manifold of FIG. 15A according to one embodiment.

FIGS. 15A-15C illustrate an impingement clamshell cooling manifold 1506 according to one embodiment of the invention. FIG. 15A shows a front view of impingement clamshell cooling manifold 1506 for impingement cooling of the microfluidic device 1412. FIG. 15B shows a transparent view of the impingement clamshell cooling manifold of FIG. 15A according to one embodiment. FIG. 15C shows airflow through the impingement clamshell cooling manifold 1506.

In the illustrated embodiment, impingement clamshell cooling manifold 1506 has a top piece 1552 and a bottom piece 1554 that can be fixed together by, for example, screw 1556 or other means described above. Microfluidic device 1412 may be inserted and removed from a compartment 1555 in the clamshell cooling manifold 1506. The compartment 1555 may be formed in the top piece 1552, the bottom piece 1554 or both the top piece 1552 and the bottom piece 1554. In the illustrated embodiment, compartment 1555 is formed in top piece 1552.

As shown in FIG. 15C, cooling air 1558 enters cooling manifold 1506 at inlet opening 1520, is directed at microfluidic device 1412 via an inlet duct 1521, impinges downwardly on the one or more heat sinks 1414 of microfluidic device 1412, and, after being heated by microfluidic device 1412, exits cooling manifold 1506 at outlet opening 1522. The inlet opening 1520, inlet duct 1521 and outlet opening 1522 may be part of (i.e., included in) the top piece 1542 of cooling manifold. However, it is possible for any of the inlet opening 1520, inlet duct 1521 and/or outlet opening 1522 to be entirely or partially part of the bottom piece 1554.

In the illustrated embodiment, when the cooling air 1558 impinges downwardly on the one or more heat sinks 1414 of microfluidic device 1412, the cooling air 1558 may impinge downwardly in a substantially vertical direction on the one or more heat sinks 1414 of microfluidic device 1412. When the cooling air 1558 exits cooling manifold 1406 at outlet opening 1522, the cooling air 1558 may exit cooling manifold 1506 in a substantially horizontal direction.

In some embodiments, one or more temperature measuring devices may be located in the cooling manifold 1506. The temperature measuring devices could be located anywhere along the manifold. In a preferred embodiment, the temperature measuring devices would be close to the heated microfluidic device so the measurement is indicative of the air temperature when it hits or flows off of the device.

In the illustrated embodiment, cooling manifold 1506 may have a first temperature measuring device 1533 located in the inlet duct 1521. First temperature measuring device 1533 may be located close to the microfluidic device 1512. Cooling manifold 1506 may have a second temperature measuring device 1537 located near outlet 1522.

Another aspect of the present invention relates the conditioning of the inlet airflow to improve the robustness of a microfluidic device, such as, for example, microfluidic device 315 or 1412, which may be a temperature sensitive device. In some lab-on-a-chip applications, temperature dependent reactions may occur on/in the microfluidic device. In some embodiments, a thermal controller, such as the thermal controller 317 illustrated in FIG. 3C, may be used to control the temperature dependent reactions on the microfluidic device. In some embodiments, the airflow used to cool the microfluidic device may be maintained at a consistent temperature. In one embodiment, the cooling air is pre-heated to a temperature that is just slightly higher than any normal ambient temperature of instrument 100. In one exemplary embodiment, the cooling air could be heated to 30 deg. C. and the instrument 100 could be specified to operate in ambient environments up to 30 deg. C.

Preheating the cooling air to a temperature that is just slightly higher than any normal ambient temperature may dramatically improved robustness. For example, in an embodiment in which PCR reactions are performed in/on the microfluidic device, preheating the cooling air to a temperature that is just slightly higher than any normal ambient temperature may result in cooling rates for the PCR reactions that are consistent regardless of ambient temperature. This may improve the specificity of the PCR. In another example, in an embodiment where precision temperature measurements are taken on the microfluidic device, having a repeatable cooling airflow with the same temperature regardless of ambient temperature ensures that temperature measurements on the microfluidic device remain under calibration conditions. In other words, more accurate on-chip temperature measurements are possible using cooling air at a temperature above a temperature range within which the ambient temperature is expected to remain.

Figure 16:
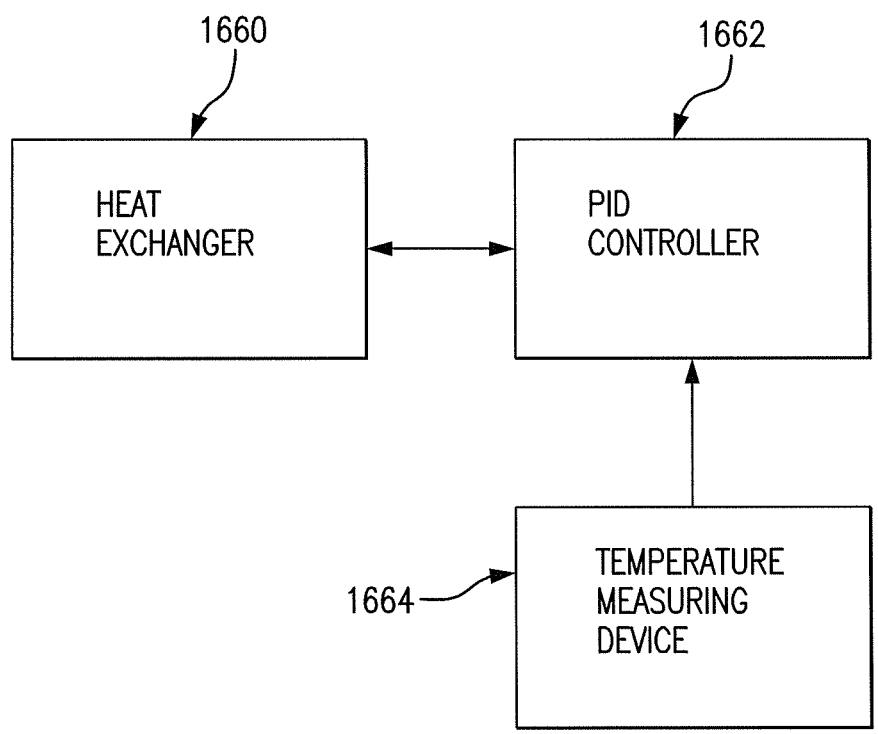
FIG. 16 depicts a preheating system according to one embodiment.

FIG. 16 illustrates a preheating system according to one embodiment of the present invention. The preheating system may include a heat exchanger 1660 that preheats the cooling airflow. The heat exchanger 1660 may be any suitable heat exchanger known in the art. The preheating may be done in conjunction with a temperature controller 1662. In the illustrated embodiment, temperature controller 1662 is a proportional—integral—derivative ("PID") controller, which may receive feedback from one or more temperature measuring devices 1664. However, other types of controllers may be used for temperature controller 1662. For example, open-loop, closed-loop, fuzzy, ON/OFF and feed forward controllers may also be used for temperature controller 1662.

In use, the one or more temperature measuring devices 1664 detects the temperature of the cooling air after it has been preheated by heat exchanger 1660. The temperature controller 1662 receives the measured temperature of the cooling air from the one or more temperature measuring devices 1664 and controls the heat exchanger to adjust the preheating so that the measured temperature of the cooling air from the one or more temperature measuring devices 1664 reaches a desired temperature. The desired temperature may be, for example, a temperature above a temperature range within which the ambient temperature is expected. The desired temperature may be adjustable or may be predetermined. In this way, the preheating system may be used to control the temperature of the cooling air provided to a microfluidic device (e.g., microfluidic device 315 or 1412).

Temperature measuring device 1664 may be any suitable device for measuring temperature. In a preferred embodiment, temperature measuring device 1664 is located in the cooling manifold. Accordingly, temperature measuring device 1664 may be, for example, any of the temperature measuring devices 733, 1333, 1433 and 1533 discussed above. However, temperature measuring device 1664 could alternatively be located elsewhere, for example, at the output of the heat exchanger or in duct 1042.

Another aspect of the present invention relates to airflow temperature measurement and uses thereof. In one embodiment, airflow temperature measurement includes measuring the inlet (i.e., cooling) airflow temperature. The measuring of inlet airflow temperature may be carried out in conjunction with preheating or without any preheating at all. The inlet airflow temperature may be measured with a suitable temperature measuring device, such as a thermistor, thermocouple, or resistance temperature detector. The inlet airflow temperature may be measured by, for example, any of the temperature measuring devices 733, 1333, 1433 and 1533 discussed above.

By measuring the input airflow temperature, the airflow temperature may be used to enhance thermal control on the microfluidic device (e.g., microfluidic device 315 or 1412). For instance, a correction (i.e., adjustment) may be provided to cooling and/or heating times and/or calibration equations that are based on the temperature measured by the inlet air flow temperature measurement. These types of corrections may be implemented as automatic (i.e., instrument controlled) corrections. For instance, the corrections may be performed by a thermal controller, such as thermal controller 317.

In one particular embodiment, a temperature measuring device (e.g., temperature measuring devices 733, 1333, 1433 and 1533) is placed within a cooling manifold where air leaves the manifold's inlet duct and is directed at a microfluidic device. The cooling manifold may be a cooling manifold in accordance with this invention (e.g., cooling manifold 106, 1306, 1406 or 1506) or any known cooling manifold. Newton's Law of cooling states that heat transfer (q) from an object is proportional to area (A) and the temperature difference between the object and the environment (T−T∞), where the proportionality constant (h) is called the heat transfer coefficient.

$$q = h * A * (T - T\infty)$$

Because the microfluidic device can be controlled, the power q is known, and, because area A and heat transfer coefficient h are fixed, only the ambient temperature T∞ of the microfluidic device is required to determine the microfluidic device temperature T. Finally, from the perspective of the microfluidic device, the ambient temperature T∞ is the temperature of the air that hits the microfluidic device. In one embodiment, a thermal controller, such as thermal controller 317, may determine the temperature T of the microfluidic device. However, in other embodiments, the temperature T of the microfluidic device may be determined by a different controller and/or off the microfluidic device. In an embodiment, where the temperature T of the microfluidic device is not determined by the microfluidic device, the determined temperature T may be transmitted to the microfluidic device (e.g., to a thermal controller that is a component of the microfluidic device).

Figure 17:
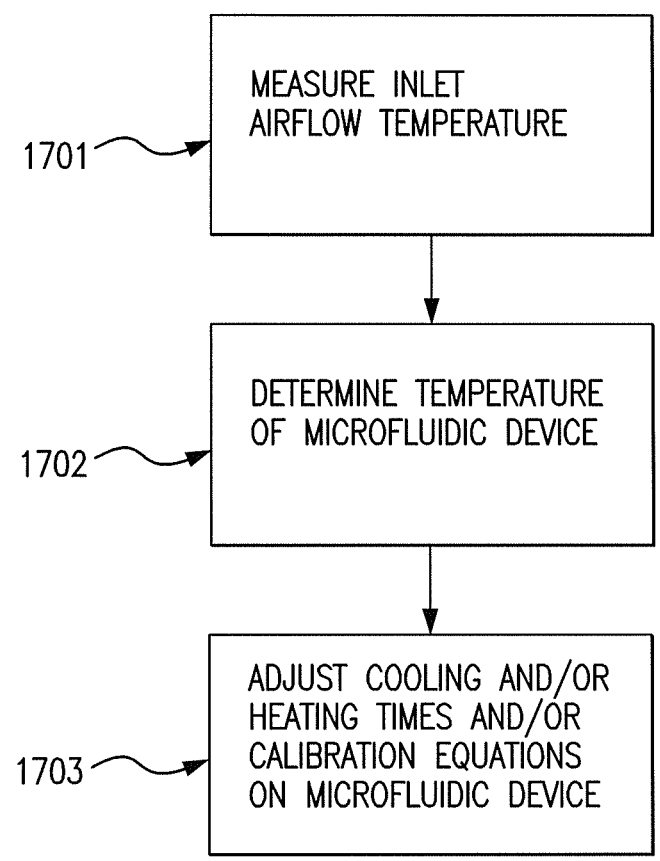
FIG. 17 is a flowchart depicting a method of measuring and using airflow temperature according to one embodiment.

FIG. 17 illustrates a method of measuring and using airflow temperature according to one embodiment. At step 1701, the inlet airflow temperature is measured. The inlet airflow temperature may be measured in any of the ways discussed above. At step 1702, the temperature of the microfluidic device is determined. The temperature of the microfluidic device may be determined based on the measured temperature of the microfluidic device in any of the ways discussed above. At step 1703, cooling and/or heating times and/or calibration equations of the microfluidic device are adjusted. The cooling and/or heating times and/or calibration equations of the microfluidic device may be adjusted based on the determined temperature of the microfluidic device.

In another embodiment of the present invention, the outlet (i.e., heated) airflow temperature is also measured. The outlet airflow temperature may be measured with a suitable temperature measuring device, such as a thermistor, thermocouple, or resistance temperature detector. The outlet airflow temperature may be measured by, for example, any of the temperature measuring devices 737, 1337, 1437 and 1537 discussed above.

The outlet airflow temperature may be used to, for example, determine the amount of power removed from the microfluidic device 315 or 1412. In this case, the amount of heat removed is the mass flow rate multiplied by the specific heat of air multiplied by the difference between the inlet and outlet air temperatures. In various embodiments, the determined amount of power removed from the microfluidic device may be used as an input to the thermal controller, a diagnostic of device performance and/or as a measure of properties of samples disposed on the microfluidic device (e.g., microchannel heat transfer rates). In one embodiment, the power removal rate may be used control the airflow and/or the pre-heating described above.

Figure 18:
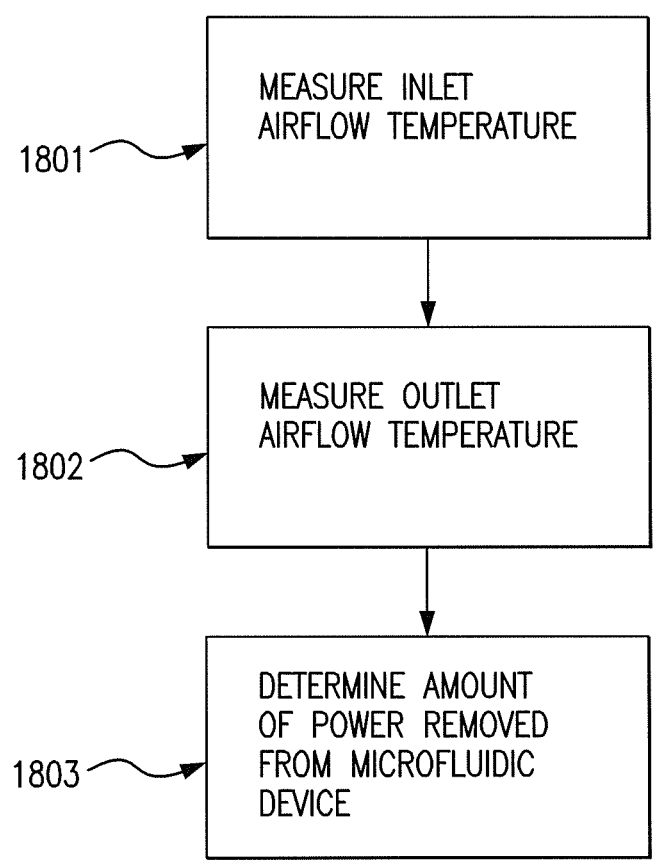
FIG. 18 is a flowchart depicting a method of measuring and using airflow temperature according to one embodiment.

FIG. 18 illustrates a method of measuring and using airflow temperature according to one embodiment. At step 1801, the inlet airflow temperature is measured. The inlet airflow temperature may be measured in any of the ways discussed above. At step 1802, the outlet airflow temperature is measured. The outlet airflow temperature may be measured in any of the ways discussed above. At step 1803, the amount of power removed from the microfluidic device is determined. The amount of power removed from the microfluidic device may be determined based on the measured inlet and outlet airflow temperatures in any of the ways discussed above.

The airflow conditioning (including preheating) and temperature measurement aspects of the invention set forth above are applicable to instruments and cooling manifolds in accordance with aspects of the present invention but are also applicable to known instruments and cooling manifolds.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:

1. A method for air cooling a microfluidic device having one or more microfluidic channels, one or more inlet ports, one or more outlet ports and one or more heat sinks, the method comprising:
   receiving cooling air through an inlet of a first duct of a bi-level cooling manifold;
   using the first duct of the cooling manifold to isolate the cooling air from the one or more inlet ports of the microfluidic device;
   directing the cooling air to a vertical channel of the first duct of the cooling manifold using an upper confinement channel of the first duct of the cooling manifold;
   directing the cooling air to the one or more heat sinks of the microfluidic device using the vertical channel of the first duct of the cooling manifold;
   heating the cooling air using the heat sinks of the microfluidic device;
   directing the heated air into a lower confinement channel of a second duct of the cooling manifold using an opening of the second duct of the cooling manifold;
   using the second duct of the cooling manifold to isolate the heated air from the one or more inlet ports of the microfluidic device; and
   directing the heated air to an outlet of the second duct using the lower confinement channel.

2. The method of claim 1, further comprising:
   using the first duct of the cooling manifold to isolate the cooling air from the one or more outlet ports of the microfluidic device; and
   using the second duct of the cooling manifold to isolate the heated air from the one or more outlet ports of the microfluidic device.

3. The method of claim 1, wherein the vertical channel of the first duct extends through the lower confinement chamber of the second duct.

4. The method of claim 1, wherein the opening comprises a first opening and a second opening, the first opening and the second opening are on opposite sides of the vertical channel of the first duct, and the directing the heated air to the outlet of the second duct using the lower confinement channel comprises directing a portion of the heated air that enters one of the first and second openings of the second duct around the vertical channel of the first duct.

5. The method of claim 1, further comprising delivering one or more liquids to the one or more inlet ports through a port of the bi-level cooling manifold.

6. The method of claim 1, further comprising measuring a temperature of the cooling air in the first duct.

7. The method of claim 6, wherein the temperature of the cooling air is measured as the cooling air leaves the vertical channel of the first duct.

8. The method of claim 6, further comprising measuring a temperature of the heated air in the second duct.

9. The method of claim 8, wherein the temperature of the cooling air is measured as the cooling air leaves the vertical channel of the first duct, and the temperature of the heated air is measured as the heated air enters the opening of the second duct.

10. The method of claim 8, further comprising determining an amount of power removed from the microfluidic device.

11. The method of claim 10, wherein the amount of power removed from the microfluidic device is determined based on the difference between the temperature of the cooling air and the temperature of the heated air.

12. The method of claim 6, further comprising determining a temperature of the microfluidic device based on the measured temperature of the cooling air in the first duct.

13. The method of claim 12, further comprising correcting cooling and/or heating times and/or calibration equations of the microfluidic device based on the determined temperature of the microfluidic device.

14. The method of claim 1, further comprising preheating the cooling air to a temperature higher than a temperature range within which an ambient temperature is expected to remain.

15. The method of claim 1, further comprising using a gasket to keep in the cooling air directed to the one or more heat sinks of the microfluidic device.

* * * * *